US011690755B2

(12) United States Patent
McGregor

(10) Patent No.: US 11,690,755 B2
(45) Date of Patent: Jul. 4, 2023

(54) CONVECTIVE DEVICE WITH PARTIALLY DETACHABLE DUCT

(71) Applicant: 3M INNOVATIVE PROPERTIES COMPANY, St. Paul, MN (US)

(72) Inventor: Andrew J. McGregor, Minneapolis, MN (US)

(73) Assignee: 3M INNOVATIVE PROPERTIES COMPANY, St. Paul, MN (US)

(*) Notice: Subject to any disclaimer, the term of this patent is extended or adjusted under 35 U.S.C. 154(b) by 640 days.

(21) Appl. No.: 15/535,610

(22) PCT Filed: Dec. 23, 2015

(86) PCT No.: PCT/US2015/000173
§ 371 (c)(1),
(2) Date: Jun. 13, 2017

(87) PCT Pub. No.: WO2016/105459
PCT Pub. Date: Jun. 30, 2016

(65) Prior Publication Data
US 2017/0360600 A1 Dec. 21, 2017

Related U.S. Application Data

(60) Provisional application No. 62/213,514, filed on Sep. 2, 2015, provisional application No. 62/096,133, filed on Dec. 23, 2014.

(51) Int. Cl.
*A61F 7/08* (2006.01)
*A61F 7/02* (2006.01)
(Continued)

(52) U.S. Cl.
CPC .............. *A61F 7/02* (2013.01); *A61F 7/0097* (2013.01); *F16L 11/121* (2013.01); *F16L 33/03* (2013.01);
(Continued)

(58) Field of Classification Search
CPC .. A61F 7/02; A61F 7/0097; A61F 2007/0091; A61F 2007/0258; A61F 2007/006; F16L 11/121; F16L 33/03
See application file for complete search history.

(56) References Cited

U.S. PATENT DOCUMENTS 4,592,576 A   6/1986  Proctor
5,261,145 A * 11/1993 Jennings ............... F16L 33/035
                                                    24/20 R
(Continued)

FOREIGN PATENT DOCUMENTS

EP        2261544 A2    12/2010
WO    WO 1998-031310     7/1998

OTHER PUBLICATIONS

International Search Report for PCT International Application No. PCT/US2015/000173, dated Apr. 19, 2016, 5 pages.

*Primary Examiner* — Kaitlyn E Smith
*Assistant Examiner* — Yasamin Ekrami
(74) *Attorney, Agent, or Firm* — Jeffrey M. Olofson

(57) ABSTRACT

At least some aspects of the present disclosure feature a convective device, comprising: a pneumatic structure formed by one or more layers, a partially detachable access duct, and a separation device disposed on a side of the partially detachable access duct. The partially detachable access duct in fluid connection with the pneumatic structure.

12 Claims, 19 Drawing Sheets

(51) Int. Cl.
*A61F 7/00* (2006.01)
*F16L 11/12* (2006.01)
*F16L 33/03* (2006.01)

(52) U.S. Cl.
CPC . *A61F 2007/006* (2013.01); *A61F 2007/0091* (2013.01); *A61F 2007/0258* (2013.01)

(56) References Cited

U.S. PATENT DOCUMENTS

| | | | |
|---|---|---|---|
| 5,792,216 A * | 8/1998 | Kappel | A61F 7/0097 5/423 |
| 6,354,099 B1 * | 3/2002 | Bieberich | A61F 7/0097 607/104 |
| 2010/0211139 A1 * | 8/2010 | Pierre | A61F 7/0097 607/104 |
| 2011/0022134 A1 | 1/2011 | Anderson | |
| 2014/0261841 A1 | 9/2014 | Orow | |
| 2014/0261844 A1 | 9/2014 | Orow | |
| 2014/0277307 A1 * | 9/2014 | Gammons | A61F 7/0097 607/107 |

* cited by examiner

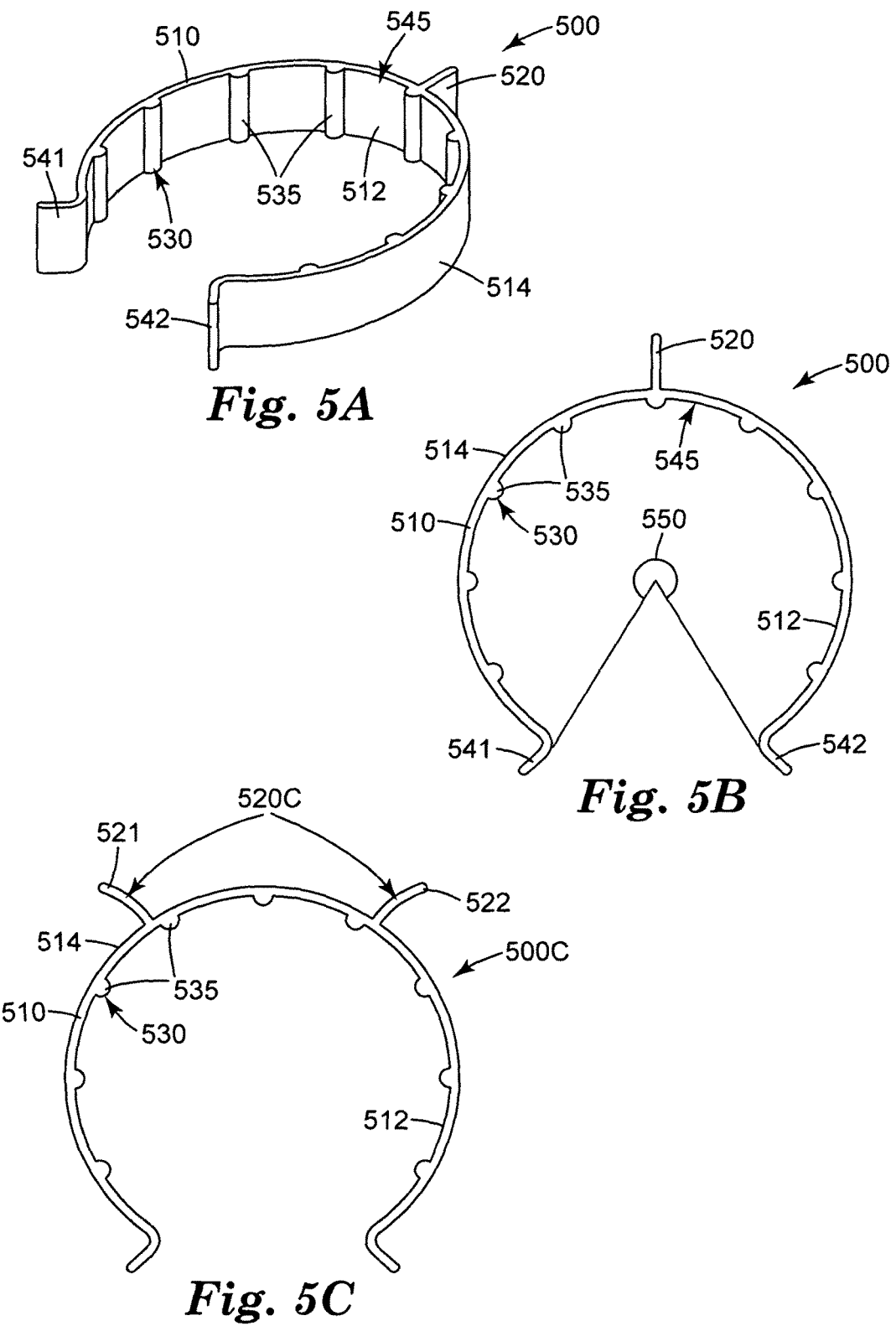

CONVECTIVE DEVICE WITH PARTIALLY DETACHABLE DUCT

CROSS REFERENCE TO RELATED APPLICATIONS

This application is a national stage filing under 35 U.S.C. 371 of PCT/US2015/000173, filed Dec. 23, 2015, which claims the benefit of U.S. Provisional Application Nos. 62/096,133, filed Dec. 23, 2014, and 62/213,514, filed Sep. 2, 2015, the disclosure of which is incorporated by reference in its/their entirety herein.

TECHNICAL FIELD

The present disclosure is related to convective systems and components to be used in a convective system for warming or cooling.

SUMMARY

At least some aspects of the present disclosure feature a convective device, comprising: a pneumatic structure formed by one or more layers, a partially detachable access duct, and a separation device disposed on a side of the partially detachable access duct. The partially detachable access duct is configured to receive a hose in connection with an inflation medium source, where the partially detachable access duct is in fluid connection with the pneumatic structure.

At least some aspects of the present disclosure feature convective system, comprising: a hose configured to connect to an inflation medium source and a convective device. The convective device includes a pneumatic structure formed by one or more layers, a partially detachable access duct, and a separation device disposed on a side of the partially detachable access duct. The partially detachable access duct is configured to receive a hose in connection with an inflation medium source, where the partially detachable access duct is in fluid connection with the pneumatic structure,

BRIEF DESCRIPTION OF DRAWINGS

The accompanying drawings are incorporated in and constitute a part of this specification and, together with the description, explain the advantages and principles of the invention. In the drawings,
FIG. 5A illustrates a perspective view of one embodiment of a hose clamp;
FIG. 5B illustrates a side view of the hose clamp illustrated in FIG. 5A;
FIG. 5C illustrates a front view of another embodiment of a hose clamp.

Figure 1A:
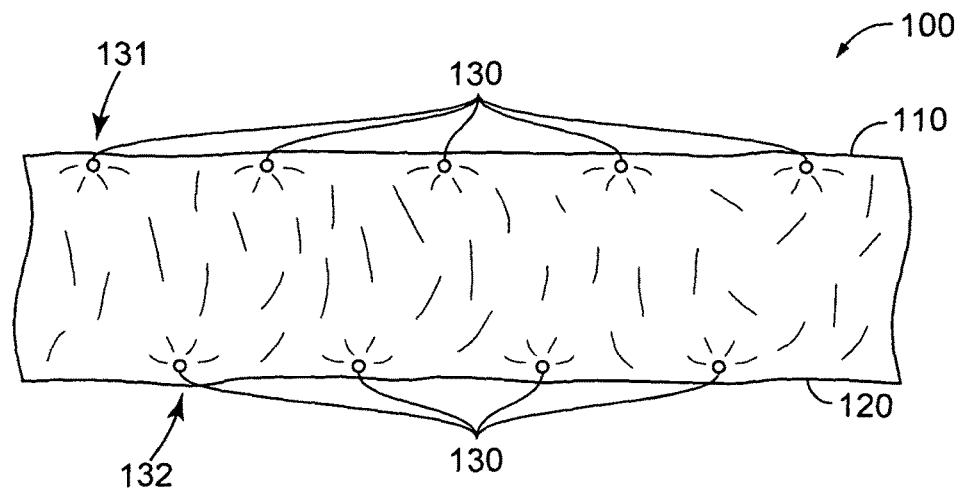
FIG. 1A illustrates one embodiment of a flexible duct.

In the drawings, like reference numerals indicate like elements. While the above-identified drawing, which may not be drawn to scale, sets forth various embodiments of the present disclosure, other embodiments are also contemplated, as noted in the Detailed Description. In all cases, this disclosure describes the presently disclosed disclosure by way of representation of exemplary embodiments and not by express limitations. It should be understood that numerous other modifications and embodiments can be devised by those skilled in the art, which fall within the scope and spirit of this disclosure.

DETAILED DESCRIPTION

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Convective devices generally refer to a device distributing matter in gas state. For example, convective devices can receive a stream of pressurized, warmed air, inflate in response to the pressurized air, distribute the warmed air within a pneumatic structure, and emit the warmed air onto a body to accomplish such objectives as increasing comfort, reducing shivering, and treating or preventing hypothermia. In some embodiments, a convective device is a tubular convective device made from blown film. In such embodiments, the convective device does not use seals to form the pneumatic structure. In some cases, the convective device includes a homogeneous material to form the pneumatic structure. In some cases, at least part of the convective device has apertures of various shapes allowing pressured fluid to go through. In some embodiments, multiple tubular convective devices with or without tear perforations are formed in a roll.

In some embodiments, a convective device has a pneumatic structure that is formed by two layers, each layer including one or more sheets, and at least one of the layers is air permeable that allows air distribution. In some cases, the two layers are formed by the same sheet(s). As used herein, "inflatable" refers to a structure which increases in volume when air or other gas is supplied at a pressure greater than atmospheric pressure to the interior of the structure. Typically these structures inflate at relatively low pressures such as pressures less than 100 mmHg, preferably at pressures less than 50 mmHg, more preferably at pressures less than 25 mmHg. In some cases, the volume of the inflatable section can increase by greater than 100%.

At least some embodiments of the present disclosure direct to a flexible duct to be used with a convective device. In some cases, the flexible duct is integrated with the convective device, which can be used as a blanket or inserted into a gown. In some cases, the flexible duct is disposable, where the duct is made of disposable materials, for example, non-woven materials, blown film, or the like. In some embodiments, the flexible duct includes air-guide device(s) to direct air when the duct is bent. Typically, the pneumatic structure of the duct is kinked or pinched off proximate to the bending area where the duct is bent. In some cases, the flexible duct further includes an air-guide device, which may include one or more air-guide elements, adapted to direct inflation medium to reduce pressure drop of the inflation medium at the bending area. For example, the flexible duct can include an air-guide device to help form one or more crease(s) when it is inflated, proximate to the air-guide device. In some embodiments, the air-guide device includes air-guide elements disposed in the pneumatic structure of the convective device. As used herein, "in" is used to describe a spatial relationship of generally in the structure including at the edge of the structure.

At least some embodiments of the present disclosure direct to a convective device having a partially detachable access duct. In some cases, the access duct allows easy connection with a hose connecting to an inflation medium source. In some embodiments, the access duct is integrated with the convective device, for example, using the same layer(s) of materials the convective device. In some embodiments, the convective device includes a separation device disposed at an edge of the access duct to partially detach the access duct from the convective device.

FIG. 1A illustrates one embodiment of a flexible duct 100. The flexible duct 100 includes an inflatable tubular structure 105 in generally a tube shape when inflated. The flexible duct is made of a flexible material 107. In some embodiments, the tubular structure 105 comprising a first longitudinal edge 110 and a second longitudinal edge 120 opposing to the first longitudinal edge 110. In some cases, an air-guide device 130 includes a plurality of air-guide elements disposed in a pattern on the tubular structure 105, where the air-guide device 130 is configured to direct flow of inflation medium when the tubular structure is bent. In the example illustrated, the air-guide element is a staked seal. In some cases, an air-guide element can be in any closed shape, for example, such as a circle, an oval, a square, a rectangle, a polygon, or the like. In some cases, an air-guide element can be a small seal in any shape, for example, such as a line, a curve, or the like. As used herein, a small seal refers to a seal having a length or diameter relative small, for example, less than two inches (5.08 cm). In some cases, the plurality of air-guide elements can be disposed with equal spacing. In some cases, at least some of the plurality of air-guide elements are disposed no more than one inch (2.54 cm) from one of the longitudinal edges. In some cases, at least some of the plurality of air-guide elements are disposed no more than two inches (5.08 cm) from one of the longitudinal edges. In some embodiments, the flexible duct 100A can include two layers of flexible materials when it is uninflated, where each layer can use a same or different material(s).

In some embodiments, the air-guide device 130 includes a first set of air-guide elements 131 disposed proximate to the first longitudinal edge 110 and a second set of air-guide elements 132 disposed proximate to the second longitudinal edge 120. In some cases, the first set of air-guide elements 131 are disposed generally equal spacing along the first longitudinal edge 110 and/or the second set of air-guide elements 132 are disposed generally equal spacing along the direction of the second longitudinal edge 120. In one embodiment, the first set of air-guide elements 131 and the second set of air-guide elements 132 are disposed in a staggered pattern.

Figure 1B:
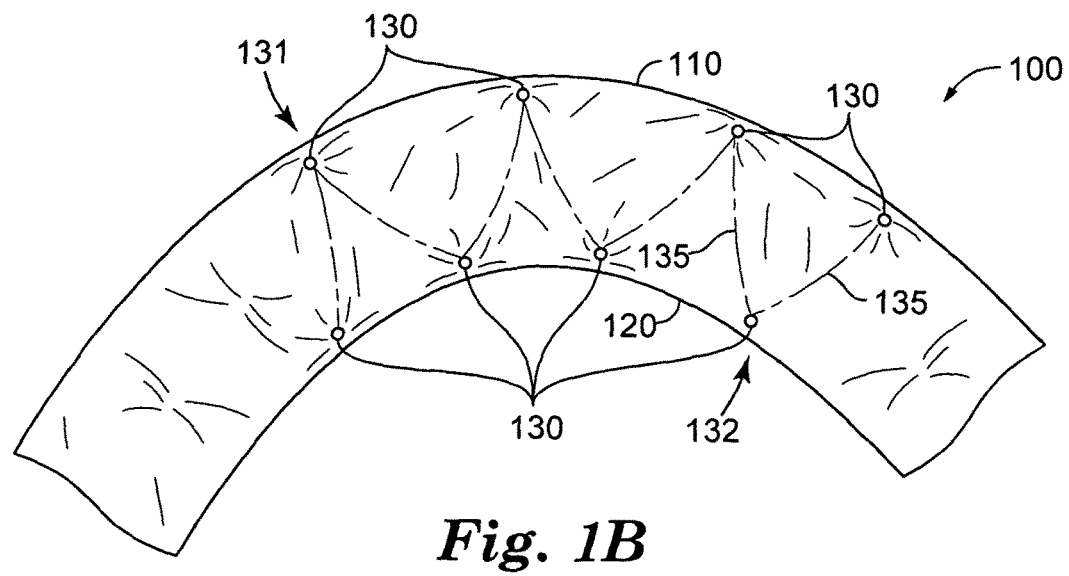
FIG. 1B illustrates a perspective view of the flexible duct illustrated in FIG. 1A when inflated and bent.

FIG. 1B illustrates a perspective view of the flexible duct 100 when inflated and bent. In some cases, the air-guide device 130 help form creases 135 proximate to the air-guide device 130 when the duct 100 is inflated and bent. In the case illustrated, creases 135 are formed between the first set of air-guide elements 131 and the second set of air-guide elements 132. A distribution of the air-guide elements may create a distribution of creases and further allow more bending areas, such that the duct becomes flexible to bend.

Figure 2A:
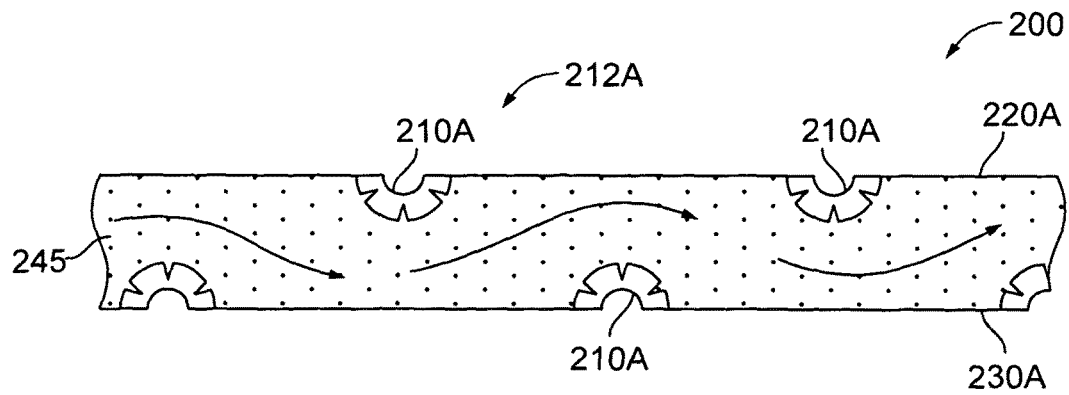
FIG. 2A illustrates one example of a flexible duct.
Figure 2B:
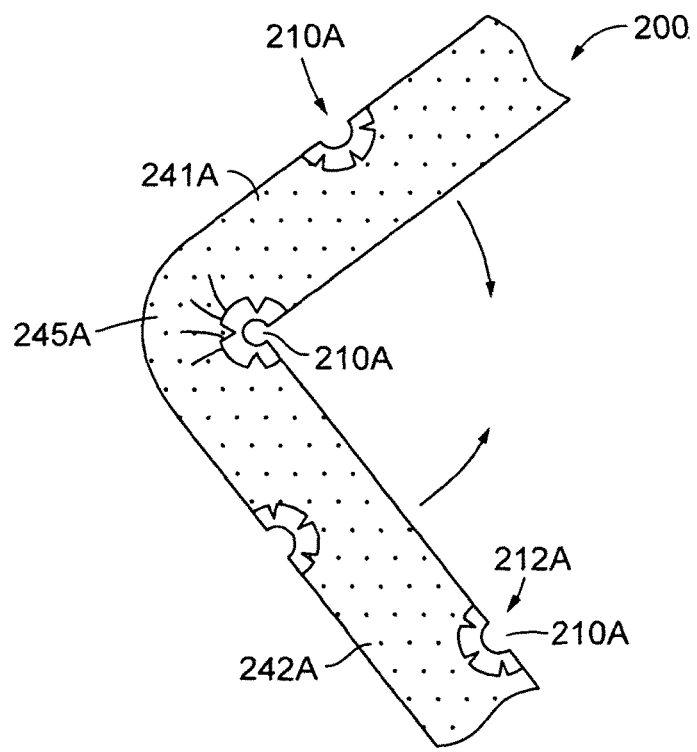
FIG. 2B illustrates the flexible duct illustrated in FIG. 2A bent at an air-guide element.

FIG. 2A illustrates one example of a flexible duct 200A. The flexible duct 200A has a first edge 220A, a second edge 230A, an inflatable channel 245A, and an air-guide device 212A including one or more air-guide elements 210A configured to direct flow of inflation medium when the flexible duct is inflated and bent. In some cases, the air-guide element 210A is disposed proximate to the first edge 220A and/or the second edge 230A. FIG. 2B illustrates the flexible duct 200A bent at one of the air-guide elements 210A, where the flexible duct 200A is separated into a first portion 241A and a second portion 242A separated at the bending location. In some cases, the air-guide element 210A is disposed in the inflatable channel 245A connecting the first portion 241A and the second portion 242A. In some cases, the air-guide element 210A is configured to facilitate forming creases, for example, 215A, at the edge of the air-guide element 210A when the flexible duct 210A is inflated and bent. In some cases, the air-guide element 210A including a guiding seal extending from an edge of the tubular flexible duct toward the tube structure.

Figure 2C:
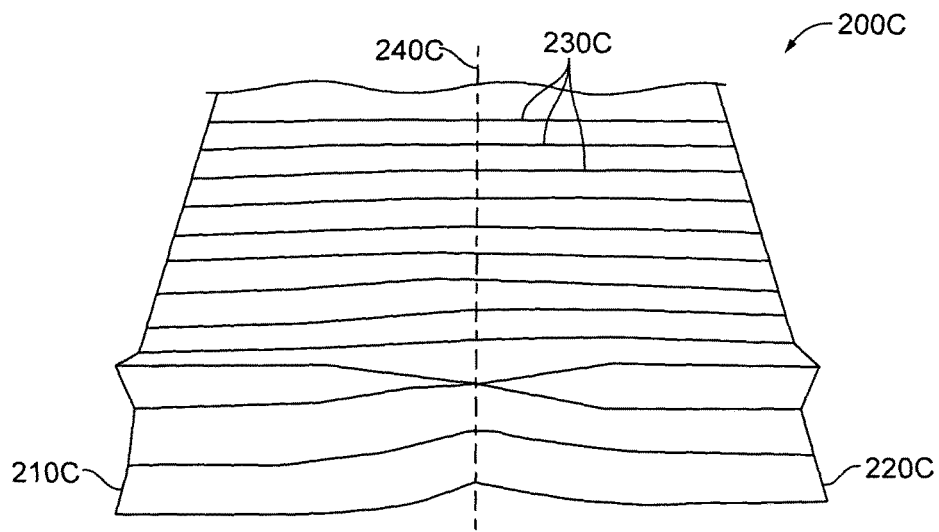
FIG. 2C illustrates another example of flexible duct.
Figure 2D:
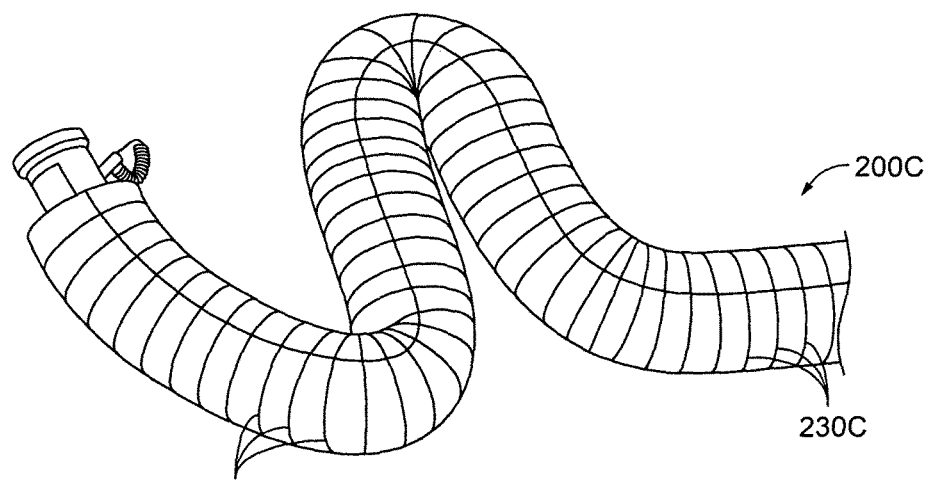
FIG. 2D illustrates a perspective view of the flexible duct illustrated in FIG. 2C being inflated and bent.

FIG. 2C illustrates a close-up view of a portion of one example of flexible duct 200C. The flexible duct 200C, as illustrated, may use a non-woven material. The duct 200C includes a plurality of pleats 230C facilitating bending. FIG. 2D illustrates a perspective view of the flexible duct 200C being inflated and bent. In some embodiments, the duct includes the z-fold pleat configuration of the duct material. The pleats are welded on each side to constrain their shape during inflation and movement. Once the pleats are formed, the edges (210C, 220C) along the longitudinal axis 240C of the duct 200C are welded or heat-sealed to hold the pleats 230C in place. One or more heat seals may be formed in the direction of the longitudinal axis 240C of the duct 200C between the two edges of the duct 200C.

Figure 2E:
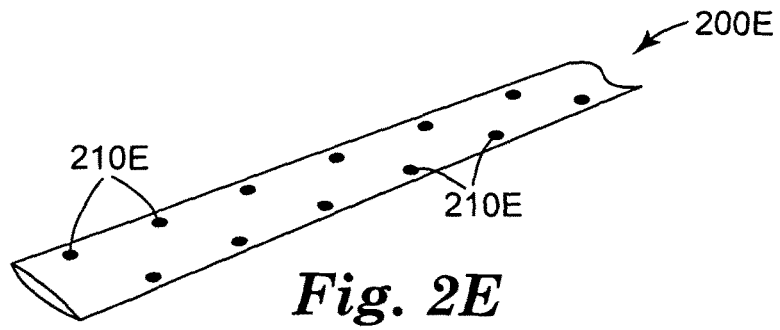
FIGS. 2E-2G illustrate some example constructions of flexible hose.
Figure 2F:
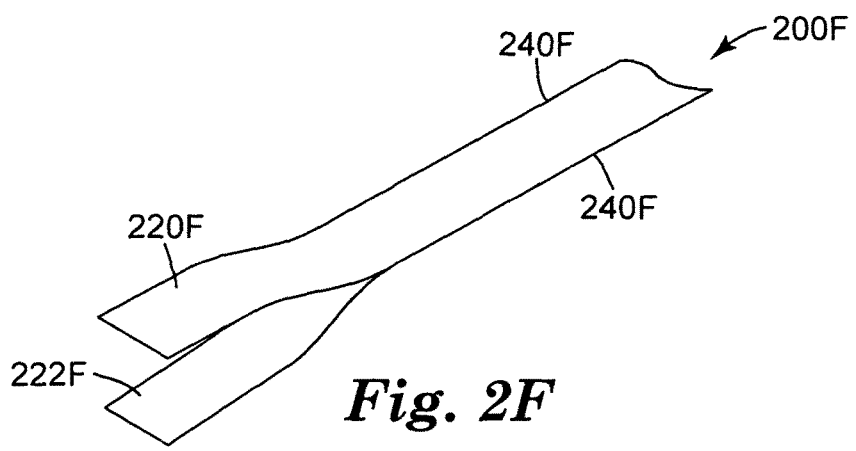
Figure 2G:
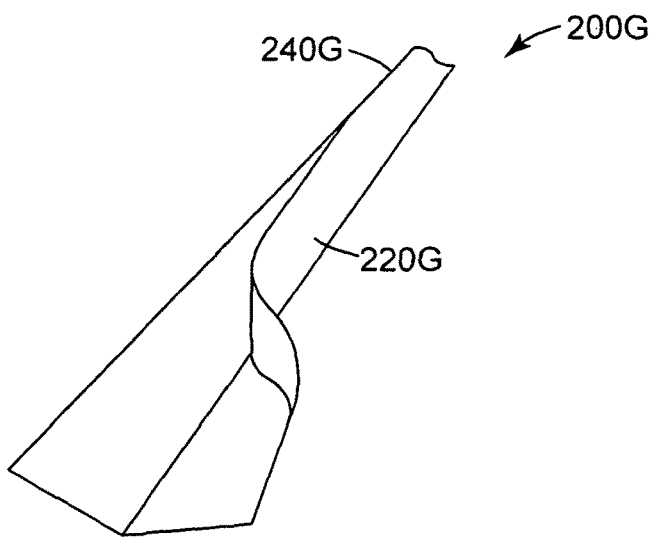

FIGS. 2E-2G illustrate some example constructions of flexible hoses. FIG. 2E illustrates a convective device 200E made from blown film, where there are no seals at the edges.

An air-guide device including a plurality of air-guide elements 210E are disposed along the edges of the duct 200E. The blown film can be made from suitable flexible polymer materials, for example, polyethylene, polyester, polypropylene (PP), high-density polyethylene (HDPE), polyethylene terephthalate (PET), polyamide (PA), or the like. The blown film is typically made from a homogeneous material.

FIG. 2F illustrates a flexible duct 200F including two layers 220F and 222F, and the two layers 220F and 222F are sealed at longitudinal edges 240F to form a pneumatic structure. In some cases, the flexible duct 200F includes an air-guide device (not illustrated). FIG. 2G illustrates a flexible duct 200G includes one layer of material 220G that is sealed at its longitudinal edge 240G. Typically, the one or more layers of the duct are made from flexible materials. In some cases, the flexible duct 200G includes an air-guide device (not illustrated).

In some implementations, the flexible duct may be integrated with a convective device. In some embodiments, a layer of a convective device may include one or more sheet of materials. In some cases, a layer of a convective device may include an underside sheet formed from a flexible, fibrous, preferably non-woven structure composed of polymeric materials capable of bonding to an upper side sheet of a heat-sealable polymeric material. For example, the underside sheet may be a non-woven, hydroentangled polyester material and the upper side layer may include a polyolefin such as a polypropylene film which is extrusion-coated, thermally laminated, or adhesively laminated onto the polyester layer. Alternatively, the underside sheet may comprise a non-woven, paper-based material to which the upper side layer, including either a polyethylene, polyester, or polypropylene film, has been glue laminated. In one embodiment, the upper side and underside sheets can be made with a stratum of absorbent tissue paper prelaminated with a layer of heat-sealable plastic. In some cases, both the first layer and the second layer can include a same polymer material.

In some embodiments, one or two layers of a flexible duct are made from a polyolefin non-woven extrusion coated, each with a coating of polypropylene on one side. In some other embodiments, the one or more layers can be poly lactic acid spunbond with polyolefin based extrusion coat. In some cases, when the convective device is assembled, the polypropylene-coated side of the first layer is sealed to the polypropylene-coated side of the second layer at the periphery, and at the one or more locations to form the construction. The sealing process can use various techniques, for example, ultrasonic welding, radio frequency welding, heat sealing, or the like. Alternatively, the first layer and second layer may each include a laminate of polypropylene and polyolefin web.

Figure 3A:
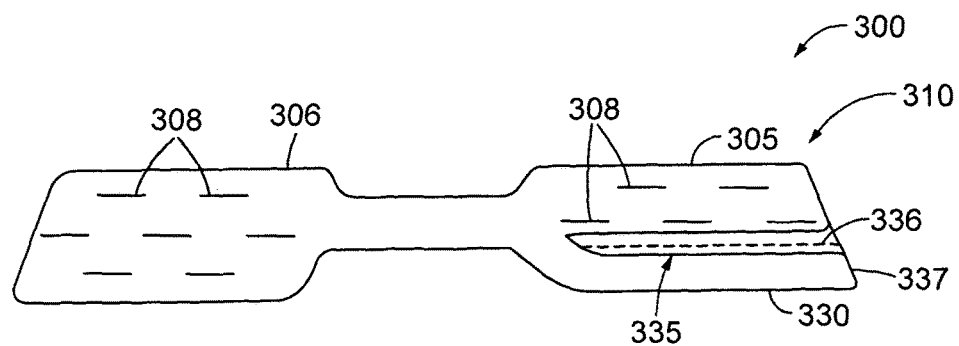
FIG. 3A shows an example of a convective device with an integrated flexible duct.
Figure 3B:
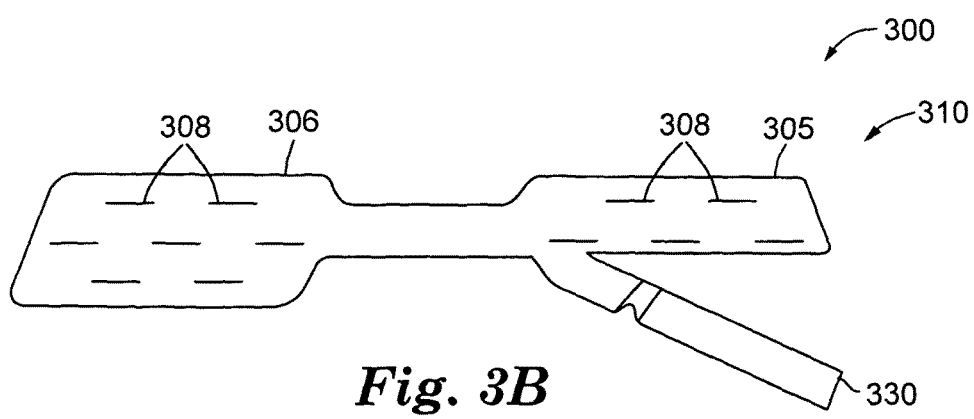
FIG. 3B shows the convective device illustrated in FIG. 3A with the flexible duct partially detached.
Figure 3C:
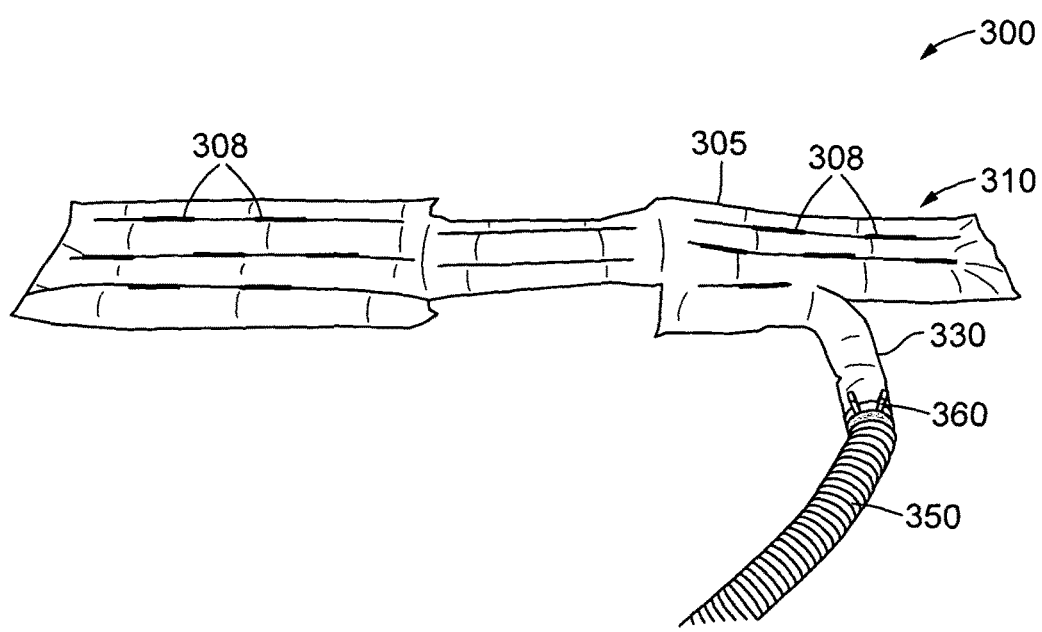
FIG. 3C shows the convective device illustrated in FIG. 3A being inflated using the flexible duct connecting to a hose.

In some cases, a flexible duct can be used with a convective device. In some other cases, a flexible duct can be integrated with a convective device. Flexible ducts can be shipped in flat packages. FIG. 3A shows an example of a convective device 300 with an integrated flexible duct 330; FIG. 3B shows the convective device 300 with the flexible duct partially detached; and FIG. 3C shows the convective device 300 being inflated using the flexible duct connecting to a hose. The convective device 300 includes a pneumatic structure 310 formed by one or more layers 305. The pneumatic structure 310 may be formed by the one or more layers 305 sealed around a periphery by a periphery seal 306. In some cases, the convective device 300 may include continuous or discontinuous seals 308, which defines air channels.

The convective device may include a separation device 335 disposed on a side of the partially detachable access duct 330. In some embodiments, the separation device 335 includes a separation element 336 and a seal 337 surrounding the separation element 336. In some cases, the separation element 336 includes, for example, at least one of a line of weakness, perforation, slit, or the like. The access duct 330 can use any configurations of flexible ducts described in the present disclosure. For example, the access duct 330 may include an air-guide device, where the air-guide device is configured to direct flow of inflation medium when the access duct is bent. As another example, the access duct may include an air-guide device, where the air-guide device includes a plurality of air-guide elements disposed proximate to one or both longitudinal edges of the access duct. The partially detachable access duct 330 is configured to receive a hose 350, as illustrated in FIG. 3C in connection with an inflation medium source (not illustrated). A hose clamp 360 may be used to maintain the connection of the access duct 330 and the hose 350. The hose clamp 360 is discussed in further details below. The partially detachable access duct 330 is in fluid connection with the pneumatic structure 310.

Figure 4A:
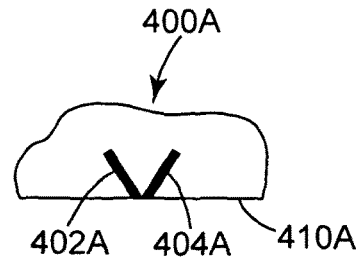
FIGS. 4A-4H illustrate some examples of air-guide elements.
Figure 4B:
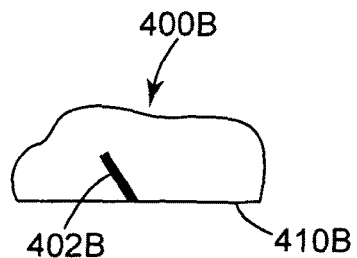
Figure 4C:
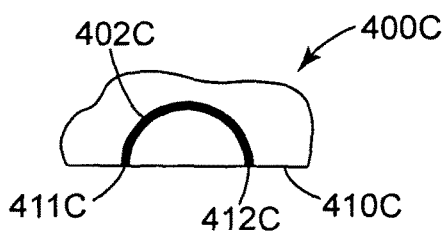
Figure 4D:
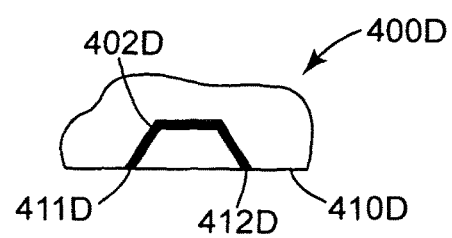

FIGS. 4A-4H illustrate some examples of air-guide devices/air-guide elements. FIG. 4A illustrates an air-guide device or air-guide element 400A including two guiding seals 402A and 404A, where both seals are extending from a periphery seal 410A. FIG. 4B illustrates an air-guide device or air-guide element 400B including one guiding seal 402B extending from a periphery seal 410B. FIG. 4C illustrates an air-guide device or air-guide element 400C including a continuous seal 402C, in a curve shape, starting from a first position 411C on a periphery seal 410C and ending at a second position 412C on the periphery seal 410C different from the first position 411C. When the convective device is inflated, the air-guide device 400C can facilitate forming a number of creases proximate to the air-guide device 400C in the convective device where the convective device is bent. FIG. 4D illustrates an air-guide device or air-guide element 400D including a continuous seal 402D starting from a first position 411D on a periphery seal 410D and ending at a second position 412D on the periphery seal 410D different from the first position 411D.

Figure 4E:
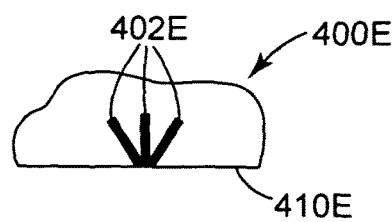
Figure 4F:
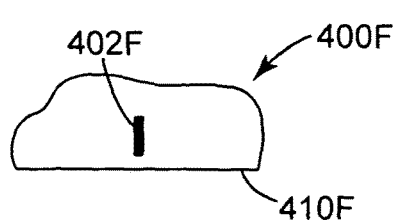
Figure 4G:
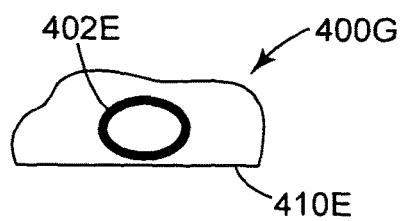

FIG. 4E illustrates an air-guide device or air-guide element 400E including three guiding seals 402E extending from a periphery seal 410E. FIG. 4F illustrates an air-guide device or air-guide element 400F including one seal 402F disposed proximate to but not touching a periphery seal 410F. FIG. 4G illustrates an air-guide device or air-guide element 400G including one continuous seal 402G in a closed shape or a closed shape seal 402G disposed proximate to but not touching a periphery seal 410G. The seal 402G can be in any closed shapes, for example, such as circle, oval, square, rectangle, polygon, or the like. In some cases, the seal 402G is no more than one inch (2.54 cm) from the periphery seal 410G. In some cases, the seal 402G is no more than two inches (5.08 cm) from the periphery seal 410G.

Figure 4H:
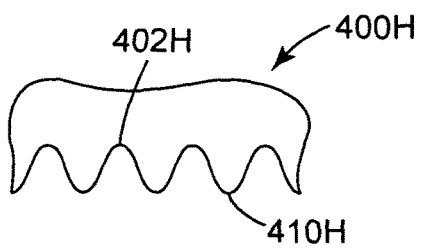

FIG. 4H illustrates an example of air-guide device 400H that is an integrated part of or proximate to a periphery seal 410H. The air-guide device 400H includes a zigzag portion 402H between first and second portions of the pneumatic structure as illustrated in FIGS. 1A, 2A and 3A, for example, such that the zigzag portion 402H is adapted to facilitate the generation of a number of distributed creases and direct inflation medium to reduce pressure drop of the inflation medium at the bending area when the configurable convective device is inflated and at least one of the first portion and the second portion are rearranged such that the air channel between the two portions is bent. In some cases, the zigzag portion 402H is integrated with the periphery seal 410H. In some cases, the entire periphery seal can be zigzagged. In some cases, the zigzag portion 402H is in a wavy shape. In some cases, the zigzag portion is a in a curve shape, square saw-tooth, triangular saw-tooth, or similar shape, or combination of shapes.

In some cases of using a flexible duct or partially detached access duct, a hose clamp may be used to maintain adequate air-tight connection between a hose connecting to an inflation medium source and the flexible duct or access duct. FIG. 5A illustrates a perspective view of one embodiment of a hose clamp 500; and FIG. 5B illustrates a side view of the hose clamp 500. In the embodiment illustrated, the hose clamp 500 includes an encircling element 510, an optional grabbing component 520 extending from the encircling element, and an optional engaging component 530 disposed on or integrated with the encircling element. The encircling element 510 includes having an inner surface 512 and an opposing outer surface 514. In some cases, the central angle 550 of the encircling element 510 is greater than 180 degree. In some cases, the central angle 550 of the encircling element 510 is smaller than 360 degree.

In some embodiments, the engaging component 530 includes a plurality of engaging elements 535. In some implementations, the engaging component 530 includes a pattern of engaging elements 535, for example, a pattern of a line, a pattern of a wave, a pattern of higher density proximate to the end, or the like. The encircling element 510 has a first end 541, a second end 542, and a middle portion 545. In some cases, the encircling element 510 can be semi-rigid or rigid. The encircling element 510 can include materials, for example, polycarbonate, polyethylene, nylon, acrylonitrile butadiene styrene (ABS), polypropylene, polyvinyl chloride (PVC), and/or the like. In some cases, the grabbing component 520 and the engaging component 530 can include the same materials as the encircling element 510. In some other cases, the grabbing component 520 and the engaging component 530 can include different materials as the encircling element 510. In some cases, the engaging component can have a material the same as or different from the material used for the encircling element 510. In some cases, the engaging component 530 can use soft materials, for example, urethane, thermoplastic materials, thermoplastic elastomers (TPE), or the like. The engaging elements 535 can have any shapes, for example, cylinder, half sphere, prism, hexagonal prism, trapezoidal prism, cube, cuboid, cone, pyramid, or the like.

FIG. 5C illustrates a front view of another embodiment of a hose clamp 500C. The hose clamp 500C includes an encircling element 510, an optional grabbing component 520C extending from the encircling element, and an optional engaging component 530 disposed on or integrated with the encircling element. Components with same labels can have same or similar configurations, compositions, functionality and/or relationships as the corresponding components in FIGS. 5A and 5B. In the embodiment illustrated, the grabbing component 520C includes two elements 521 and 522.

Figure 6A:
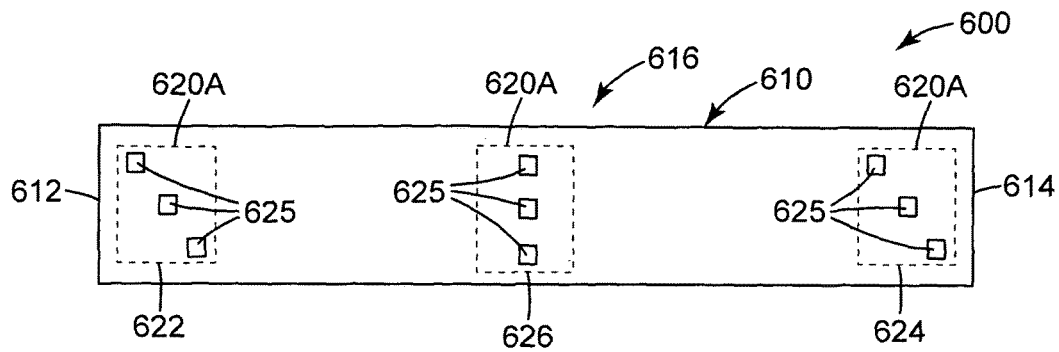
FIG. 6A is a flattened view of a hose clamp toward the inner surface of an encircling element.
Figure 6B:
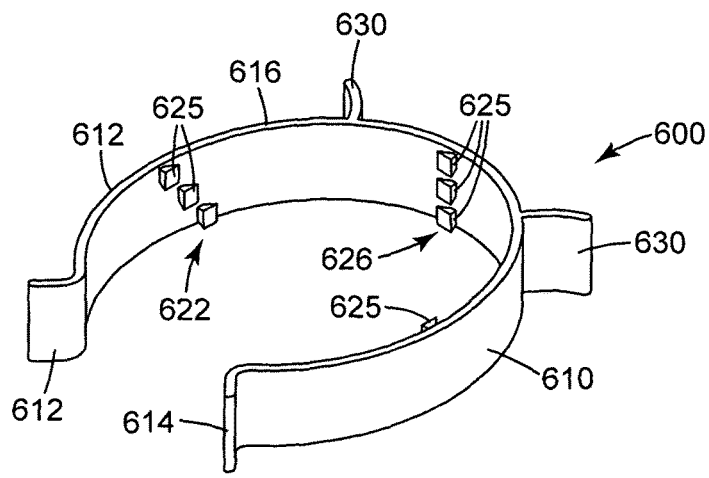
FIG. 6B is a perspective view of the hose clamp illustrated in FIG. 6A.
Figure 6C:
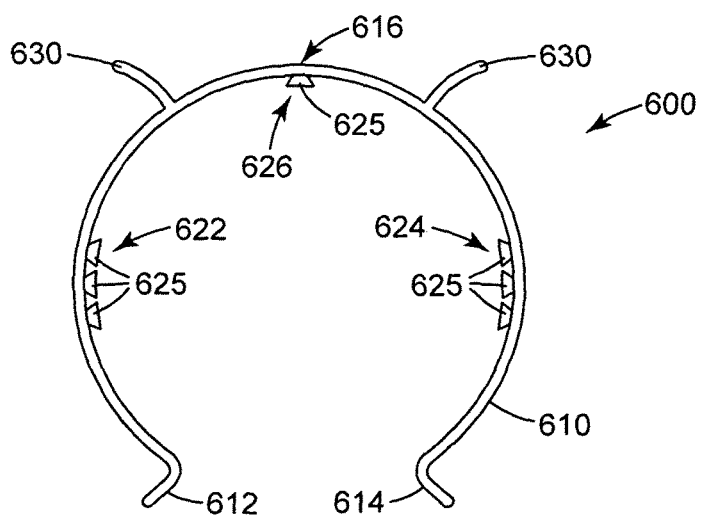
FIG. 6C is a side view of the hose clamp illustrated in FIG. 6A.

FIG. 6A is a flattened view of a hose clamp 600 toward the inner surface of an encircling element; FIG. 6B is a perspective view of the hose clamp 600; and FIG. 6C is a side view of the hose clamp 600. The hose clamp 600 includes an encircling element 610, an optional grabbing component 630 and an optional engaging component 620A. The encircling element 610 has a first end 612, a second end 614, and a middle portion 616. The engaging component 620A can include one or more sets of engaging elements 625. In one embodiment, the engaging component 620A includes a set of engaging elements 622 disposed proximate to the first end 612 of the encircling element 610. In the example illustrated in 6A, the set of engaging elements 622 includes multiple engaging elements 625 (with three illustrated) disposed in a line, where the engaging elements 625 are disposed in a line slanted from the first end 612. In some embodiments, the engaging component 620A includes a set of engaging elements 624 disposed proximate to the second end 614 of the encircling element 610. In the example illustrated in FIG. 6A, the set of engaging elements 624 includes multiple engaging elements 625 disposed in a line, where the engaging elements 625 are disposed in a line slanted from the second end 614. In some embodiments, the engaging component 620A includes a set of engaging elements 626 disposed in the middle portion 616. In some cases, the set of engaging elements 626 includes at least three engaging elements 625 disposed in a line.

Figure 6D:
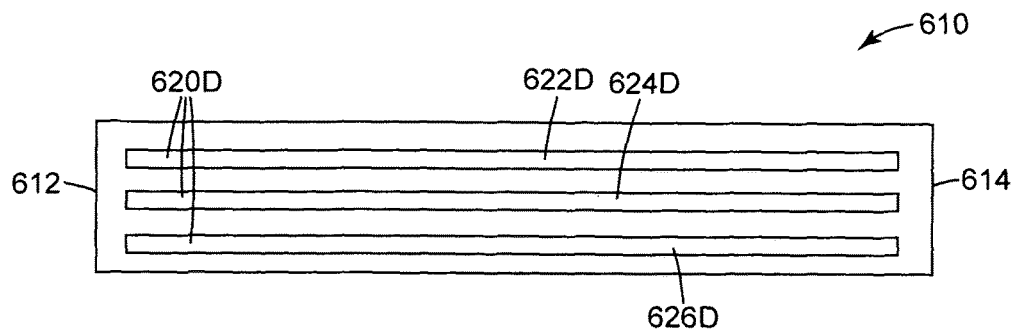
FIGS. 6D-6G illustrate some example configurations of engaging components.
Figure 6E:
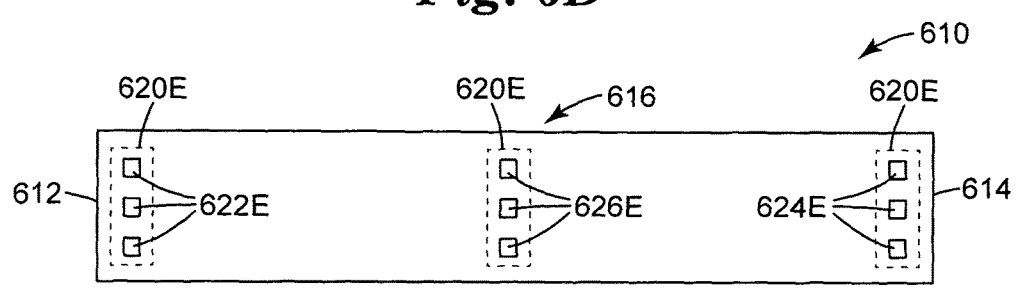

FIGS. 6D-6G illustrate some example configurations of engaging components. FIG. 6D illustrates an engaging component 620D includes three elongated engaging elements 622D, 624D, and 626D that are generally parallel with each other and extend proximate the first end 612 to the second end 614. FIG. 6E illustrates an engaging component 620E includes three sets of engaging elements (622E, 624E, and 626E). The set of engaging element 622E is proximate to the first end 612 and is in a line. The set of engaging element 624E is proximate to the second end 614 and is generally in a line. The set of engaging element 626E is proximate to the center portion 616 and is generally parallel to either end.

Figure 6F:
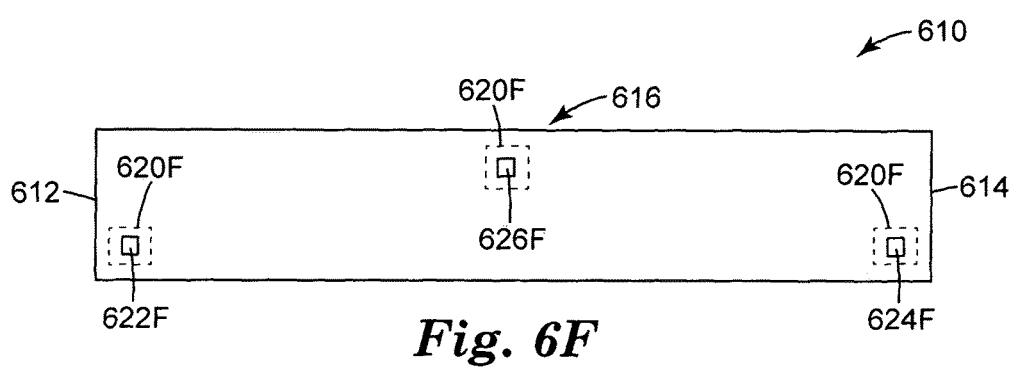
Figure 6G:
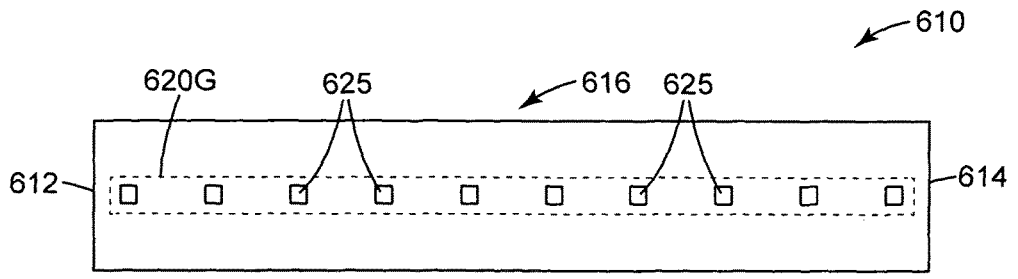

FIG. 6F illustrates an engaging component 620F including three engaging elements (622F, 624F, and 626F). The engaging element 622F is disposed proximate to the first end 612, the engaging element 624F is disposed proximate to the second end 614, and the engaging element 626F is disposed at the center portion 616. The three engaging elements 622F, 624F, and 626F, as illustrated, may be disposed at locations with different distances to the edges of the encircling element 610. FIG. 6G illustrates an engaging component 620G including multiple engaging elements 625. In one embodiment, the engaging elements 625 can be disposed discontinuously across the encircling element 610 from the first end 612 to the second end 614.

Figure 7A:
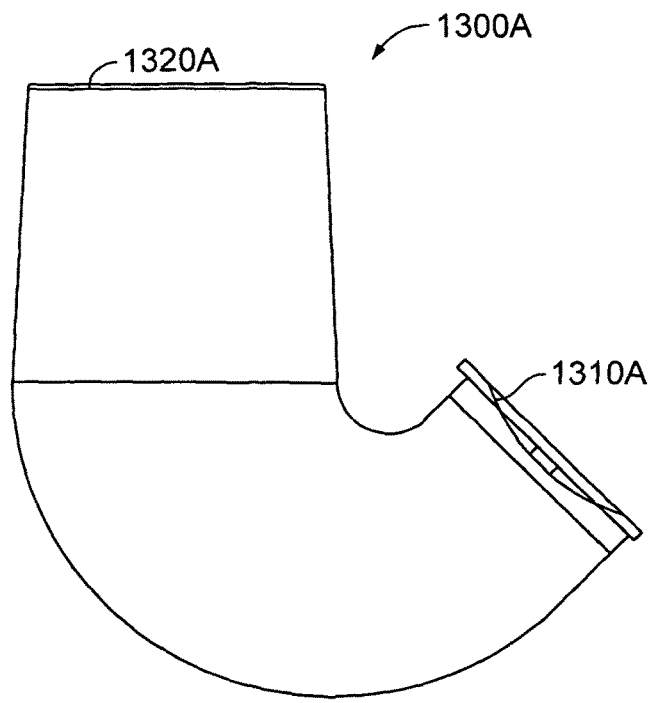
FIGS. 7A-7N illustrate some examples of nozzle configurations.
Figure 7B:
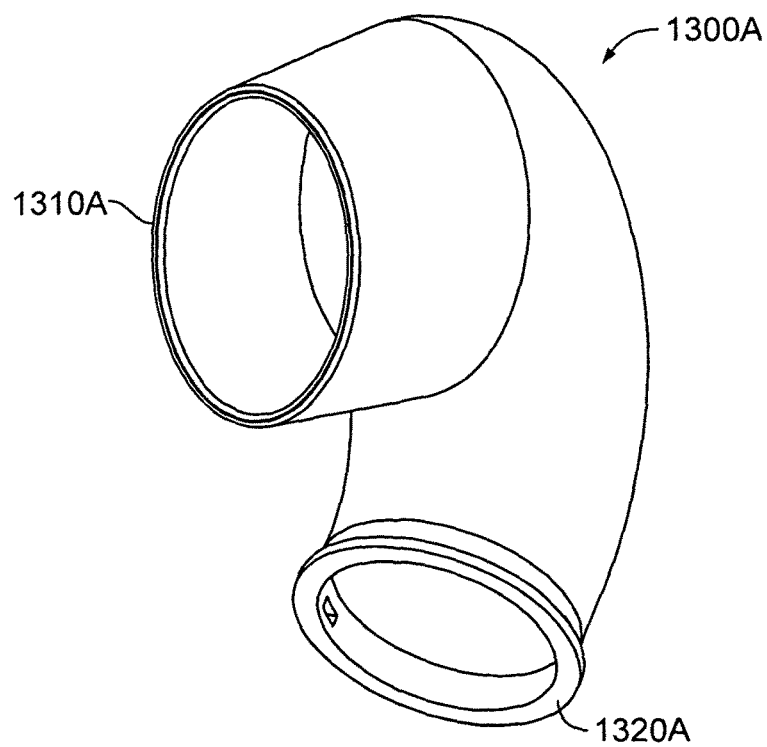

In some embodiments, a convective system includes an inflation medium source, a convective device, and a hose connecting the inflation medium source and the convective device. The convective device includes a pneumatic structure and an opening into the pneumatic structure. The hose includes a nozzle to insert to the opening of the convective device. The convective device can use any embodiments of convective device described herein. FIGS. 7A-7N illustrate some examples of nozzle configurations. FIG. 7A illustrates a side view of a nozzle 1300A; and FIG. 7B illustrates a perspective view of the nozzle 1300A facing the end of the nozzle. In the embodiment illustrated, the nozzle 1300A is generally in a J-shape. The nozzle 1300A includes a first end 1310A and a second end 1320A. In addition, the cross section of the first end 1310A is elliptical. In some embodiments, the cross section of the second end 1320A is generally circular. In some cases, the nozzle 1330A may include a hindrance device (not shown), for example, a raised-up, to fix connection between the nozzle and the convective device. The hook portion proximate to the first end 1310A can have various angles from the support portion proximate to the second end 1320A, for example, 0-90 degree, and various lengths.

Figure 7C:
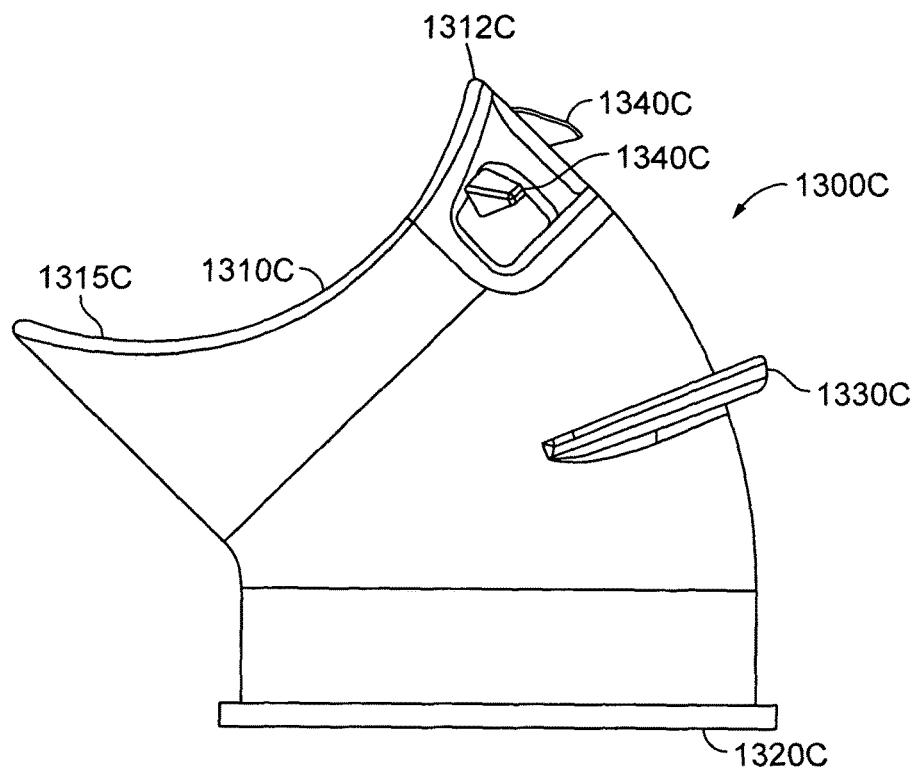
Figure 7D:
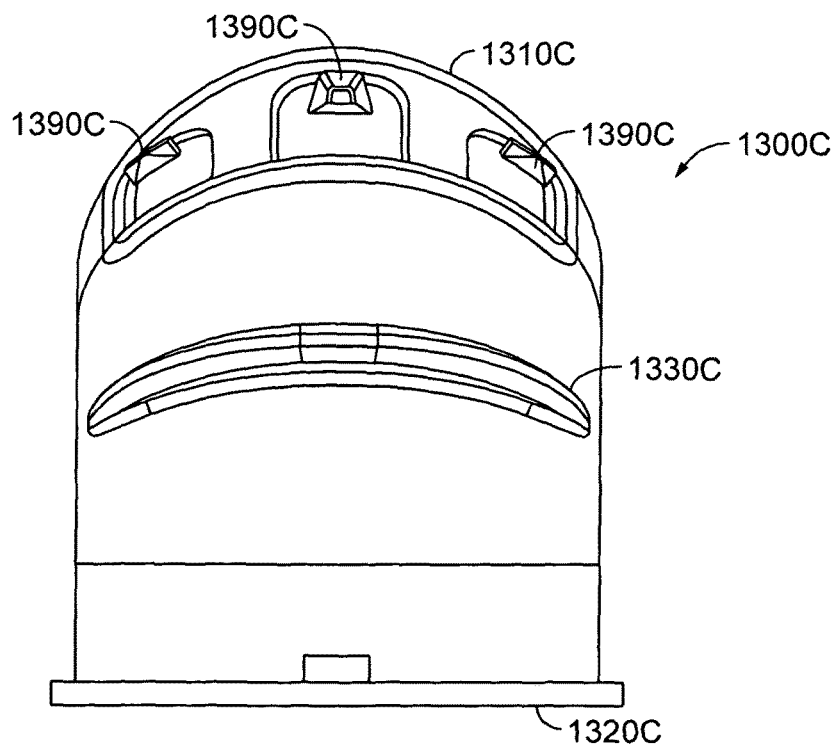
Figure 7E:
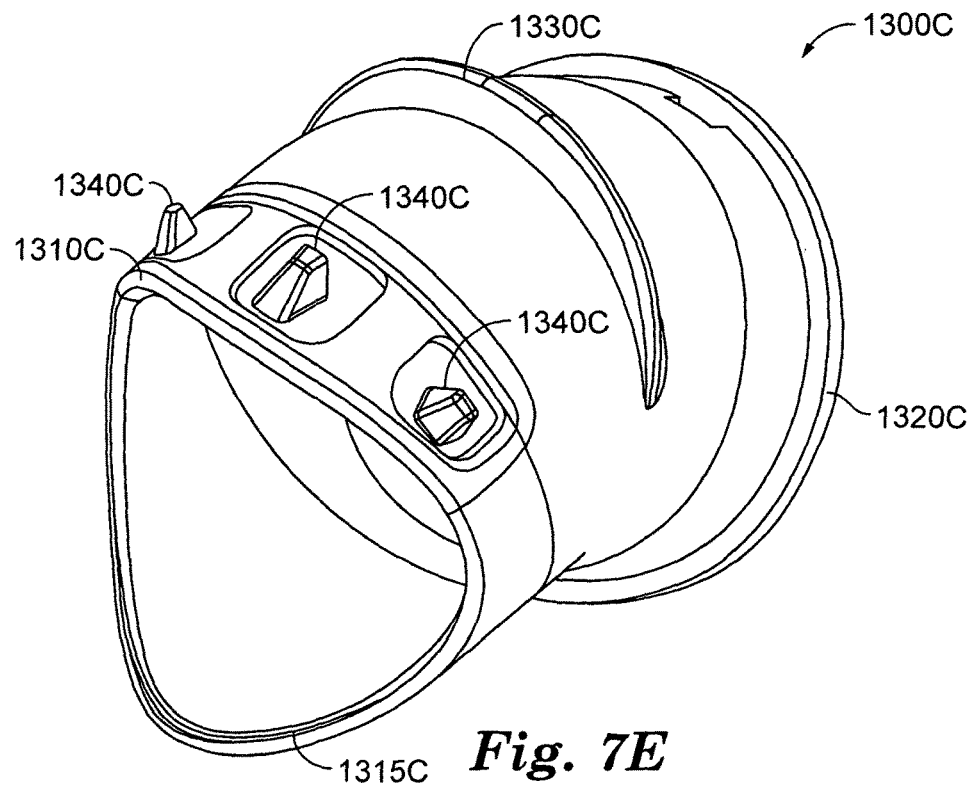

FIG. 7C illustrates a side view of a nozzle 1320C; FIG. 7D illustrates another side view of the nozzle 1320C; and FIG. 7E illustrates a perspective view of the nozzle 1300C facing one end of the nozzle. The nozzle 1300C includes a main body 1305C, a first end 1310C and a second end 1320C, where the first end 1310C is to be inserted into the opening of the convective device. In some cases, the nozzle main body 1305C includes one or more vents (not shown) allowing air to go through. The nozzle 1300C includes a hindrance device 1330C disposed on the nozzle. In some cases, the hindrance device 1330C is configured to prevent the nozzle from over insertion. In some configurations, the hindrance device 1330C is disposed on a portion or all of the circumference of the nozzle 1300C.

In some embodiments, the hindrance device 1330C comprises a softer material than the material of the nozzle. In some cases, the hindrance device 1330C may include soft or rigid thermoplastic elastomers such as polyesters, polyurethanes, polyamides, or polyolefin blends; or thermoset elastomers such as natural and synthetic rubbers such as latex, nitrile, millable polyurethane, silicone, butyl and neoprene. In the example illustrated, the hindrance device 1330C is disposed along the circumference of the nozzle 1300C. In some embodiments, the nozzle 1300C includes a piercing device 1340C disposed on the nozzle 1300C. In this example, the piercing device 1340C comprises a plurality of piercing elements 1345C, where each piercing element 1345C is a protruded from the nozzle main body 1305C. In some cases, the piercing element 1345C has a slope in cross-sectional view with a lower protrusion closer to the first end 1310C and a higher protrusion farther from the first end 1310C. In some cases, the piercing device 1340C is configured to facilitate insertion and/or prevent the hose from slipping from the opening of the convective device. In some cases, the piercing device 1340C is disposed closer to the first end 1310C than the hindrance device 1330C. In some cases, at least one of the piercing elements 1345C is in the shape of trapezoidal prism. In some cases, at least one of the piercing elements 1345C is in the shape of triangular prism. In some configurations, the nozzle 1300C includes a protrusion portion 1315C at the first end 1310C.

Figure 7F:
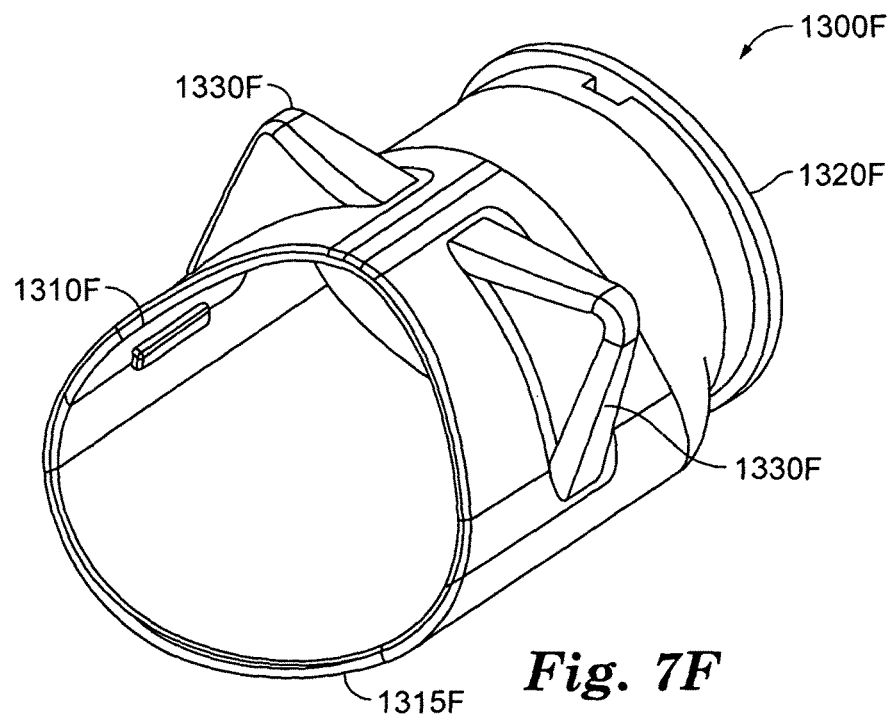
Figure 7G:
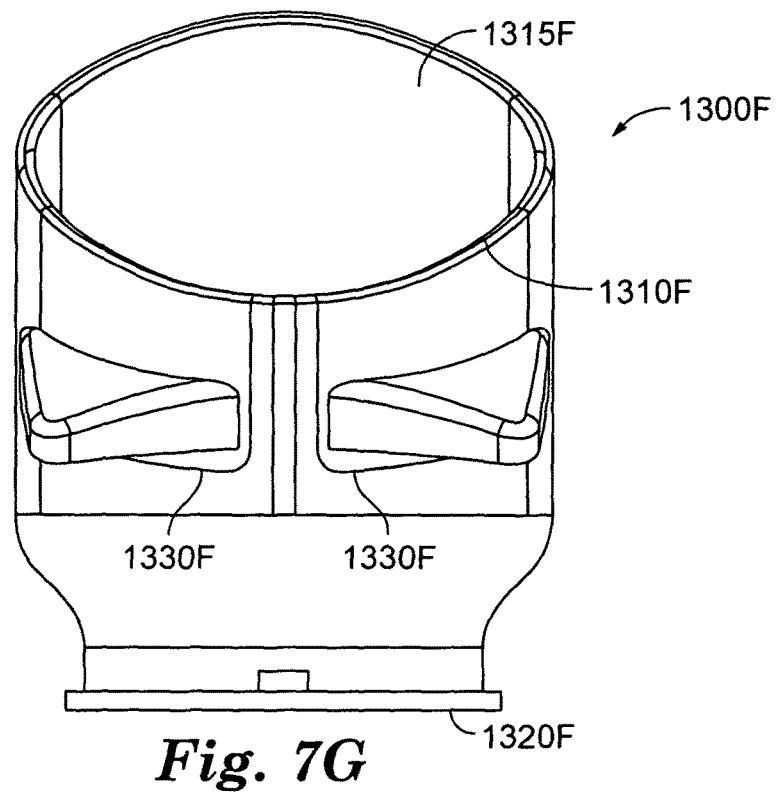
Figure 7H:
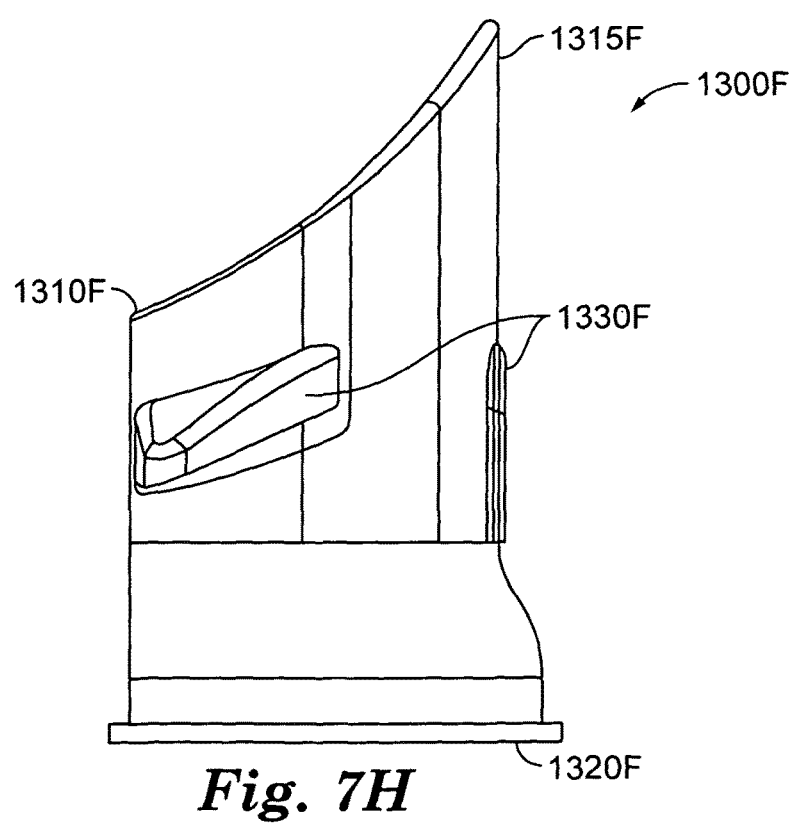

FIG. 7F illustrates a perspective view of a nozzle 1320F from one end; FIG. 7G illustrates a side view of the nozzle 1320F; and FIG. 7H illustrates another side view of the nozzle 1300F. The nozzle 1300F includes a main body 1305F, a first end 1310F and a second end 1320F, where the first end 1310F is to be inserted into the opening of the convective device. The hose includes a hindrance device 1330F disposed on the nozzle. In some cases, the hindrance device 1330F is configured to prevent the nozzle from over insertion. In some configurations, the hindrance device 1330F is disposed on a portion of a circumference of the nozzle 1300F. In the example illustrated, the hindrance device 1330F includes a plurality of hindrance elements 1335F disposed in a pattern on the nozzle 1300F. In some implementations, a cross section of each of the hindrance elements 1335F is generally triangular. In some configurations, the nozzle 1300F includes a protrusion portion 1315F at the first end 1310F.

Figure 7I:
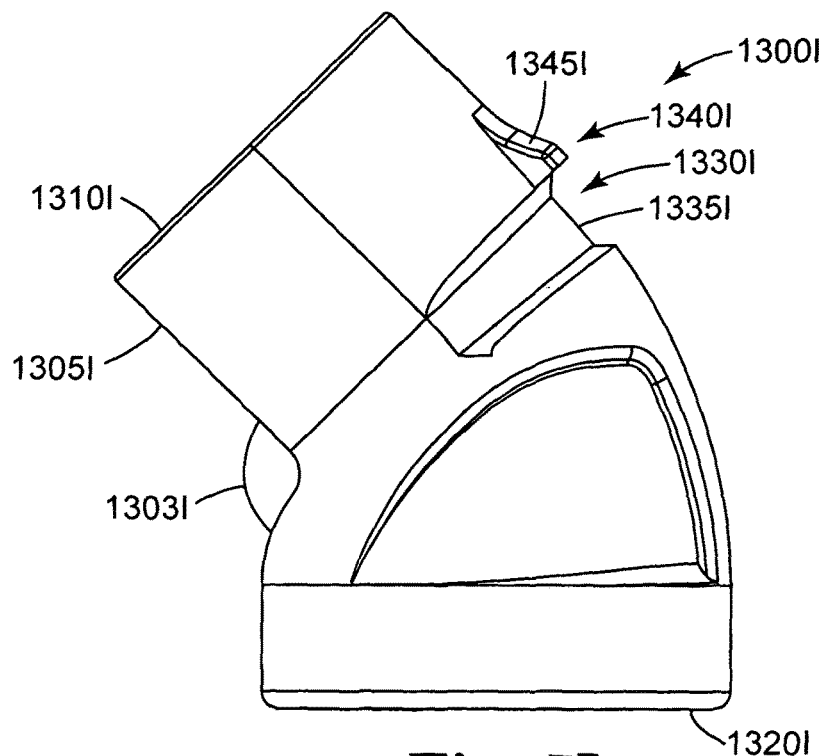
Figure 7J:
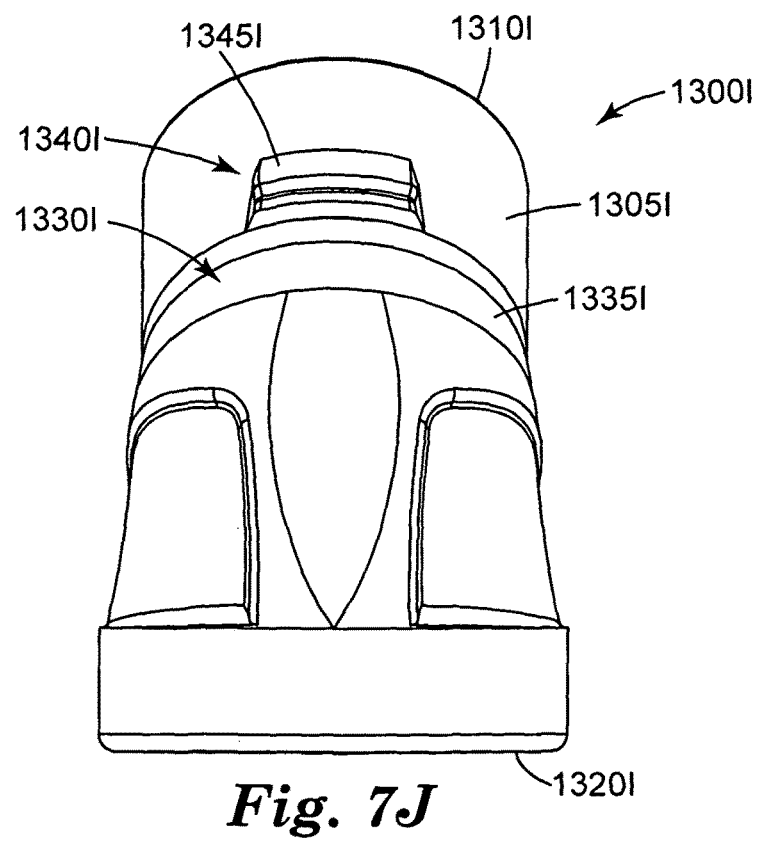
Figure 7K:
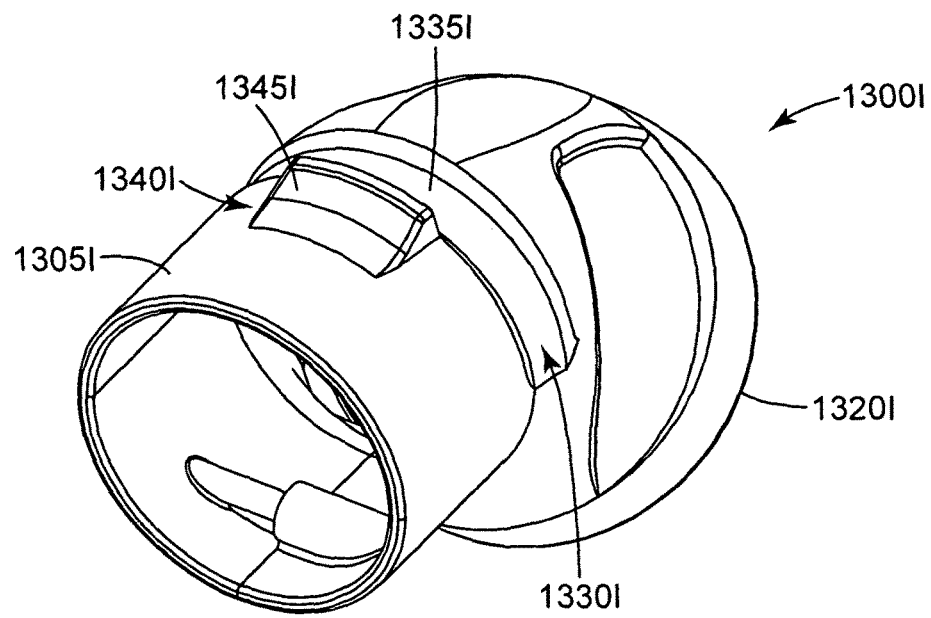

FIG. 7I illustrates a side view of a nozzle 1320I; FIG. 7J illustrates another side view of the nozzle 1320I; and FIG. 7K illustrates a perspective view of the nozzle 1300I facing one end of the nozzle. The nozzle 1300I includes a main body 1305I, a first end 1310I and a second end 1320I, where the first end 1310I is to be inserted into the opening of the convective device. In some cases, the nozzle main body 1305I includes one or more vents (not shown) allowing air to go through. In some cases, the nozzle main body 1305I has an angle 1303I between the two portions of the main body. The nozzle 1300I includes a hindrance device 1330I integrated with the nozzle main body, for example, by having a recess portion 1335I. In some cases, the hindrance device 1330I is configured to prevent the nozzle from over insertion. In some configurations, the hindrance device 1330I is integrated with a portion or all of the circumference of the nozzle 1300I, where the recess 1335I extends a portion or all of the circumference of the nozzle 1300I.

In some embodiments, the nozzle 1300I includes a piercing device 1340I disposed on the nozzle 1300I. In this example, the piercing device 1340I comprises a plurality of piercing elements 1345I, where the piercing element 1345I is a protruded from the nozzle main body 1305I. In some cases, the piercing element 1345I has a slope in cross-sectional view with a lower protrusion closer to the first end 1310I and a higher protrusion farther from the first end 1310I. In some cases, the piercing device 1340I, maybe together with the recess portion 1335I, is configured to facilitate insertion and/or prevent the hose from slipping from the opening of the convective device. In some cases, the piercing device 1340I is disposed closer to the first end 1310I than the hindrance device 1330I. In some cases, a piercing element 1345I is in the shape of trapezoidal prism. In some cases, a piercing element 1345I is in the shape of triangular prism.

Figure 7L:
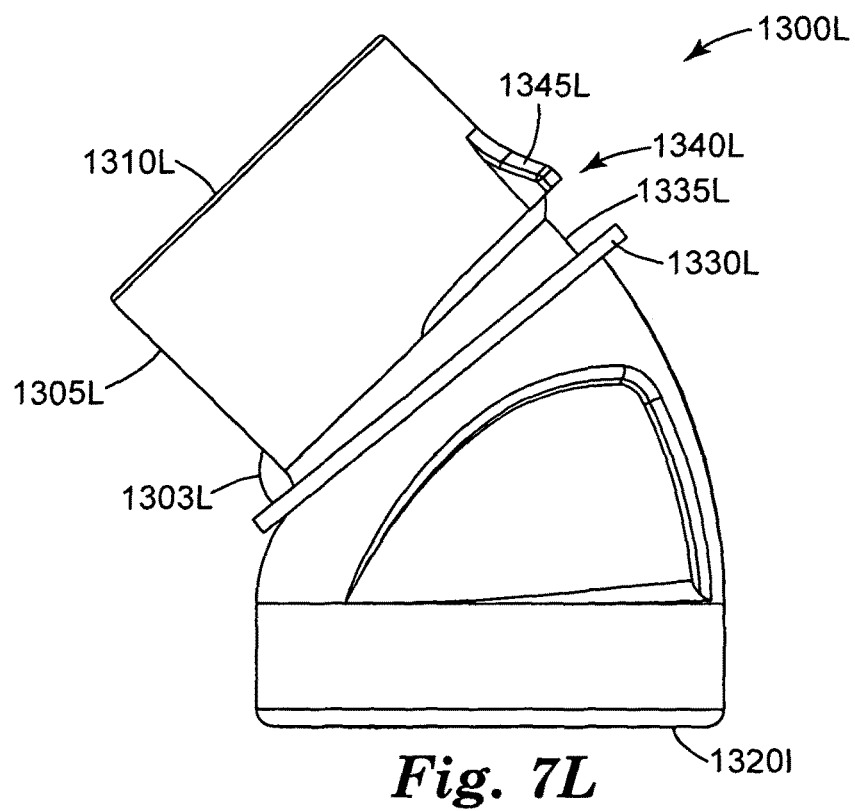
Figure 7M:
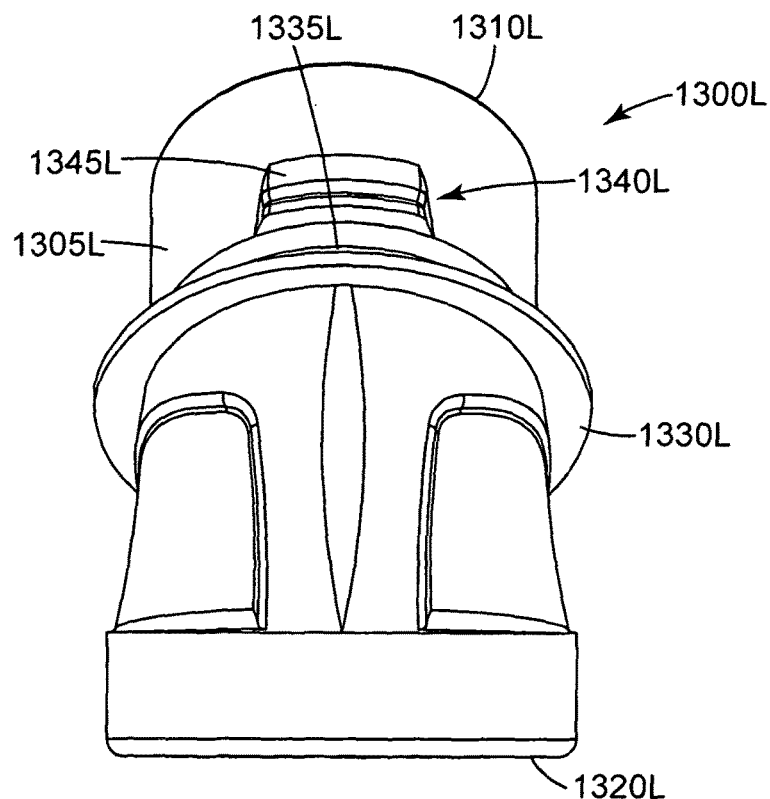
Figure 7N:
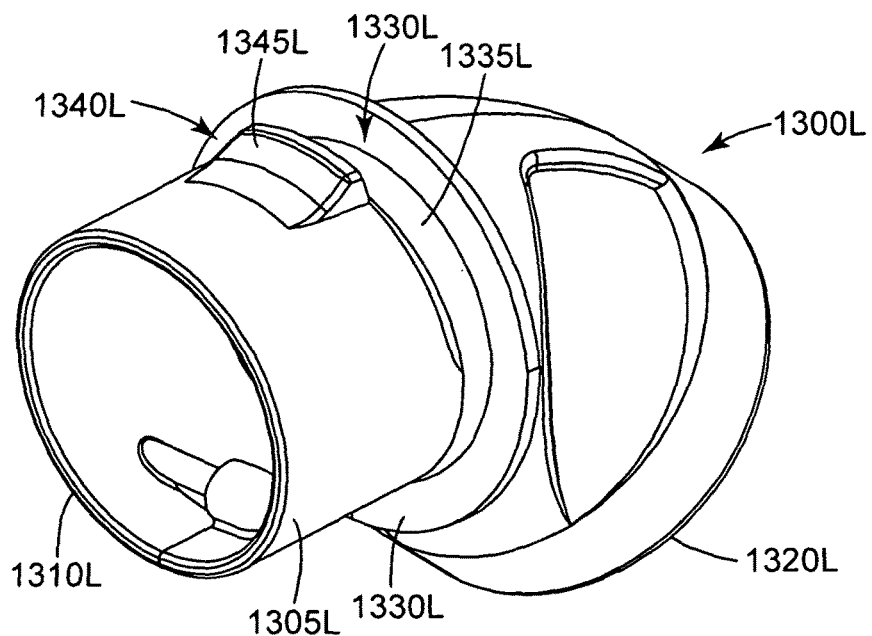

FIG. 7L illustrates a side view of a nozzle 1320L; FIG. 7M illustrates another side view of the nozzle 1320L; and FIG. 7N illustrates a perspective view of the nozzle 1300L facing one end of the nozzle. The nozzle 1300L includes a main body 1305L, a first end 1310L and a second end 1320L, where the first end 1310L is to be inserted into the opening of the convective device. In some cases, the nozzle main body 1305L includes one or more vents (not shown) allowing air to go through. In some cases, the nozzle main body 1305L has an angle 1303L between the two portions of the main body. The nozzle 1300L includes a hindrance device 1330L protruded from the nozzle main body 1305L. In some cases, the nozzle 1300L includes a recess portion adjacent to the hindrance device 1330L. In some cases, the hindrance device 1330L is configured to prevent the nozzle from over insertion. In some configurations, the hindrance device 1330L is disposed on a portion or all of the circumference of the nozzle 1300L, where the recess 1335L extends a portion or all of the circumference of the nozzle 1300L.

In some embodiments, the hindrance device 1330L comprises a softer material than the material of the nozzle. In some cases, the hindrance device 1330L may include soft or rigid thermoplastic elastomers such as polyesters, polyurethanes, polyamides, or polyolefin blends; or thermoset elastomers such as natural and synthetic rubbers such as latex, nitrile, millable polyurethane, silicone, butyl and neoprene. In the example illustrated, the hindrance device 1330L is disposed along the circumference of the nozzle main body 1305L. In some embodiments, the nozzle 1300L includes a piercing device 1340L disposed on the nozzle 1300L. In this example, the piercing device 1340L comprises one or more piercing elements 1345L, where the piercing element 1345L is a protruded from the nozzle main body 1305L. In some cases, the piercing element 1345L has a slope in cross-sectional view with a lower protrusion closer to the first end 1310L and a higher protrusion farther from the first end 1310L. In some cases, the piercing device 1340L is configured to facilitate insertion and/or prevent the hose from slipping from the opening of the convective device. In some cases, the piercing device 1340L is disposed closer to the first end 1310L than the hindrance device 1330L. In some cases, a piercing element 1345L is in the shape of trapezoidal prism. In some cases, a piercing element 1345L is in the shape of triangular prism.

Figure 8A:
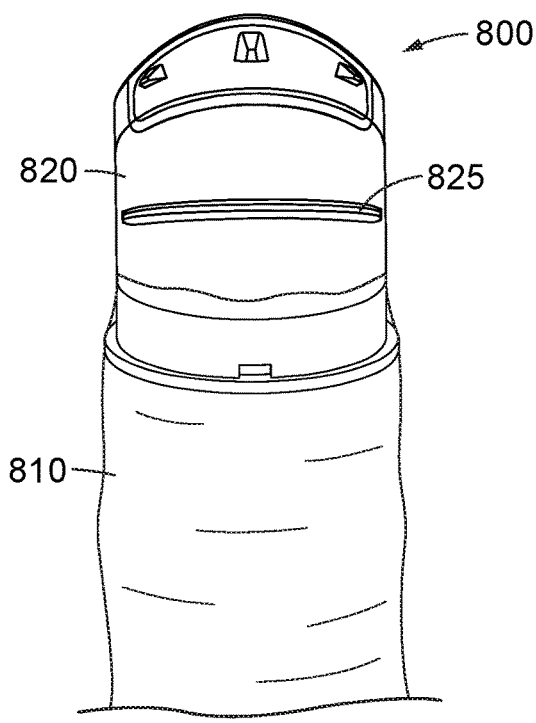
FIGS. 8A, 8B, and 8C illustrate an example of a convective system using a flexible duct.
Figure 8B:
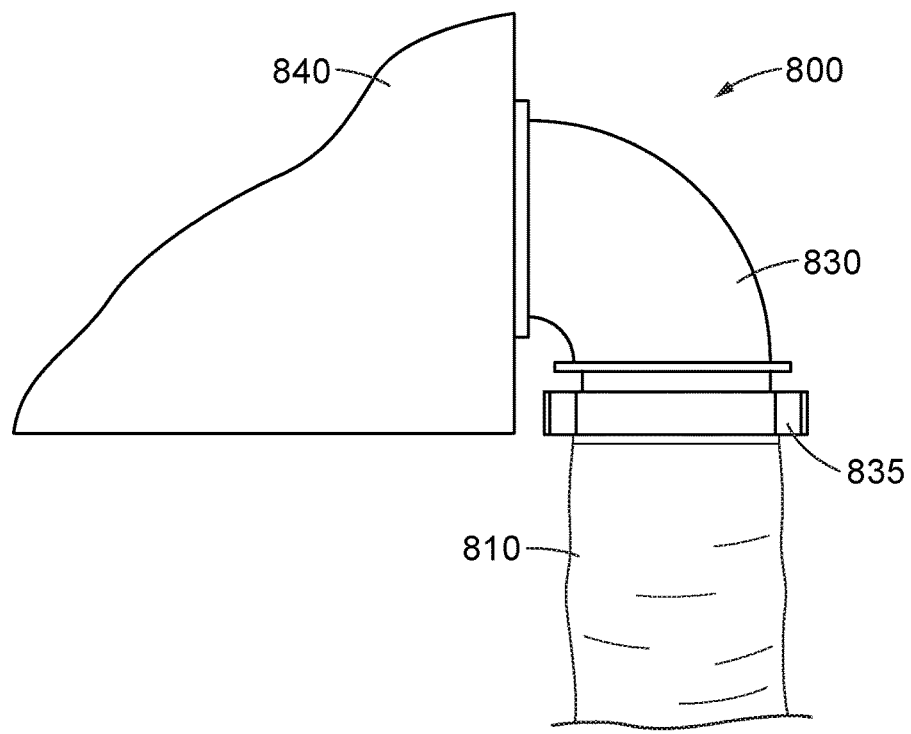
Figure 8C:
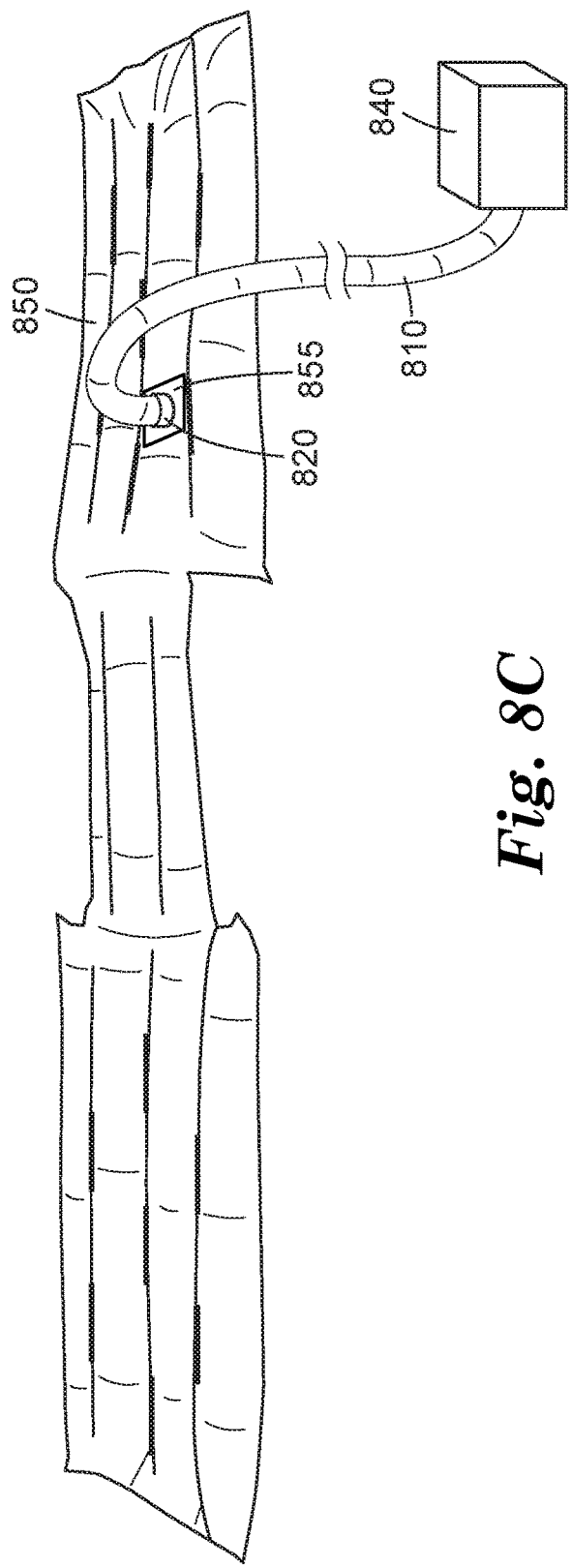

FIGS. 8A, 8B, and 8C illustrate an example of a convective system 800 using a flexible duct. The convective system includes a flexible duct 810, which is connected to a nozzle 820 at one end. In some cases, the nozzle 820 may include a hindrance device 825 to prevent over insertion of the nozzle. FIG. 8B illustrates the flexible duct 810 connecting to an inflation medium source 840 via a nozzle 830. In this example, the flexible duct 810 is connected to the nozzle 830 with a hose clamp 835. The flexible duct, nozzle, and hose clamp may use any configuration of flexible ducts, nozzles, and hose clamps described in the present disclosure. FIG. 8C illustrates the flexible duct 810 is connected to a convective device 850 via an opening 855 in the convective device 850. The nozzle 820 is inserted into the opening 855.

Exemplary Embodiments

Item A1. A flexible duct for a convective device, comprising:
  an inflatable tubular structure in generally a tube shape when inflated comprising a flexible material, the tubular structure having a first longitudinal edge and a second longitudinal edge opposing to the first longitudinal edge; and
  an air-guide device comprising a plurality of air-guide elements disposed in a pattern on the tubular structure, wherein the air-guide device is configured to direct flow of inflation medium when the tubular structure is bent.

Item A2. The flexible duct of Item A1, wherein the air-guide device comprises staked seals.

Item A3. The flexible duct of Item A1 or A2, wherein the air-guide device comprises a first set of air-guide elements disposed proximate to the first longitudinal edge.

Item A4. The flexible duct of Item A3, wherein the first set of air-guide elements are disposed generally equal spacing along the first longitudinal edge.

Item A5. The flexible duct of Item A3, wherein the air-guide device further comprises a second set of air-guide elements disposed proximate to the second longitudinal edge.

Item A6. The flexible duct of Item A5, wherein the first set of air-guide elements are disposed generally equal spacing along the first longitudinal edge and the second set of air-guide elements are disposed generally equal spacing along the second longitudinal edge.

Item A7. The flexible duct of any one of Item A1-A6, wherein the first set of air-guide elements and the second set of air-guide elements are disposed in a staggered pattern.

Item A8. The flexible duct of any one of Item A1-A7, wherein the tubular structure comprises two flexible layers sealed along the first and the second longitudinal edges.

Item A9. The flexible duct of any one of Item A1-A8, wherein the tubular structure comprises one flexible layer sealed along the first longitudinal edge.

Item A10. The flexible duct of any one of Item A1-A9, wherein the flexible duct is disposable.

Item A11. A convective system, comprising:
  a convective device comprising a pneumatic structure and an opening,
  a disposable duct comprising:
    an inflatable tubular structure in generally a tube shape when inflated comprising a flexible material, and
    an air-guide device disposed in the tubular structure, and
  a nozzle configured to connect to the disposable duct,
  wherein the opening is configured to receive the nozzle.

Item A12. The convective system of Item A11, wherein the air-guide device comprises a plurality of air-guide elements disposed in a pattern on the tubular structure, wherein the air-guide device is configured to direct flow of inflation medium when the tubular structure is bent.

Item A13. The convective system of Item A11 or A12, wherein the air-guide device comprises staked seals.

Item A14. The convective system of any one of Item A11-A13, wherein the air-guide device comprises a first set of air-guide elements disposed proximate to a first longitudinal edge of the inflatable tubular structure.

Item A15. The convective system of Item A14, wherein the first set of air-guide elements are disposed generally equal spacing along the first longitudinal edge.

Item A16. The convective system of Item A14, wherein the air-guide device further comprises a second set of air-guide elements disposed proximate to a second longitudinal edge of the inflatable tubular structure opposing to the first longitudinal edge.

Item A17. The convective system of Item A16, wherein the first set of air-guide elements are disposed generally equal spacing along the first longitudinal edge and the second set of air-guide elements are disposed generally equal spacing along the second longitudinal edge.

Item A18. The convective system of Item A17, wherein the first set of air-guide elements and the second set of air-guide elements are disposed in a staggered pattern.

Item A19. The convective system of any one of Item A11-A18, wherein the tubular structure comprises a blown film.

Item A20. The convective system of any one of Item A11-A20, wherein the tubular structure comprises one flexible layer sealed along the first longitudinal edge.

Item A21. The convective system of any one of Item A11-A20, wherein the flexible duct is disposable.

Item B1. A convective device, comprising:
  a pneumatic structure formed by one or more layers,
  a partially detachable access duct configured to receive a hose in connection with an inflation medium source, the partially detachable access duct in fluid connection with the pneumatic structure, and
  a separation device disposed on a side of the partially detachable access duct.

Item B2. The convective device of Item B1, wherein the separation device comprises a separation element and a seal surrounding the separation element.

Item B3. The convective device of Item B1 or B2, wherein the separation element comprises at least one of a line of weakness, perforation, and slit.

Item B4. The convective device of any one of Item B1-B3, wherein the access duct comprises an air-guide device disposed in the access duct, wherein the air-guide device is configured to direct flow of inflation medium when the access duct is bent.

Item B5. The convective device of Item B4, wherein the air-guide device comprises a plurality of staked seals.

Item B6. The convective device of Item B5, wherein at least part of the staked seals are disposed proximate to a longitudinal edge of the access duct.

Item B7. The convective device of Item B6, wherein at least part of the staked seals are disposed generally equal spacing along the longitudinal edge.

Item B8. A convective system, comprising:
  a convective device, comprising:
    a pneumatic structure formed by one or more layers,
    a partially detachable access duct configured to receive a hose in connection with an inflation medium source, the partially detachable access duct in fluid connection with the pneumatic structure, and
    a separation device disposed on a side of the partially detachable access duct.

Item B9. The convective system of Item B8, wherein the separation device comprises a separation element and a seal surrounding the separation element.

Item B10. The convective system of Item B8 or B9, wherein the separation element comprises at least one of a line of weakness, perforation, and slit.

Item B11. The convective system of any one of Item B8-B10, wherein the access duct comprises an air-guide device disposed in the access duct, wherein the air-guide device is configured to direct flow of inflation medium when the access duct is bent.

Item B12. The convective system of Item B11, wherein the air-guide device comprises a plurality of staked seals.

Item B13. The convective system of Item B12, wherein at least part of the staked seals are disposed proximate to a longitudinal edge of the access duct.

Item B14. The convective system of Item B13, wherein at least part of the staked seals are disposed generally equal spacing along the longitudinal edge.

Item B15. The convective system of any one of Item B8-B14, further comprising:
  a hose configured to connect to an inflation medium source;
  a hose clamp, comprising:
    an encircling element, and
    a grabbing component extending from the encircling element;
  wherein the hose is configured to connect to the access duct, wherein the hose clamp is configured to use at the connection of the access duct and the hose.

Item B16. The convective system of Item B15, wherein the encircling element has a first end and a second end, and wherein the engaging component comprises a first set of engaging elements disposed proximate to the first end.

Item B17. The convective system of Item B16, wherein the engaging component further comprises a second set of engaging elements disposed proximate to the second end.

The present invention should not be considered limited to the particular examples and embodiments described above, as such embodiments are described in detail to facilitate explanation of various aspects of the invention. Rather the present invention should be understood to cover all aspects of the invention, including various modifications, equivalent processes, and alternative devices falling within the spirit and scope of the invention as defined by the appended claims and their equivalents.

What is claimed is:

1. A convective device, comprising:
  a pneumatic structure formed by one or more layers,
  a tubular structure configured to be partially detached, extending from a first end to an opposing second end, wherein the tubular structure is detachable from the pneumatic structure and configured to receive a hose in connection with an inflation medium source at the first end, and wherein the second end of the tubular structure is in fluid connection with the pneumatic structure, and
  a separation element comprising at least one of a line of weakness, perforation, and slit disposed on a side of the tubular structure between the tubular structure and the pneumatic structure, the separation element extending from the first end to the second end,
  wherein the tubular structure comprises an air-guide device disposed in the tubular structure, wherein the air-guide device is configured to direct flow of inflation medium when the tubular structure is bent,
  wherein the air-guide device is disposed proximate to and no more than one inch (2.54 cm) from a longitudinal edge of the tubular structure forming one or more creases proximate to the air-guide device when the tubular structure is inflated.

2. The convective device of claim 1, wherein the separation element comprises a seal surrounding the separation element.

3. The convective device of claim 1, wherein the air-guide device comprises a plurality of staked seals extending from a periphery seal.

4. The convective device of claim 3, wherein at least part of the staked seals are disposed proximate to the longitudinal edge of the tubular structure.

5. The convective device of claim 4, wherein at least part of the staked seals are disposed generally equal spacing along the longitudinal edge.

6. A convective system, comprising:
  a hose configured to connect to an inflation medium source;
  a convective device, comprising:
    a pneumatic structure formed by one or more layers,
    a tubular structure configured to be partially detached, extending from a first end to an opposing second end, wherein the first end of the tubular structure is detachable from the pneumatic structure and configured to receive the hose at the first end, and wherein the second end of the tubular structure is in fluid connection with the pneumatic structure, and
    a separation element comprising at least one of a line of weakness, perforation, and slit disposed on a side of the tubular structure between the tubular structure and the pneumatic structure, the separation element extending from the first end to the second end,
    wherein the tubular structure comprises an air-guide device disposed in the tubular structure, wherein the air-guide device is configured to direct flow of inflation medium when the tubular structure is bent,
    wherein the air-guide device is proximate to and disposed no more than one inch (2.54 cm) from a longitudinal edge of the tubular structure forming one or more creases proximate to the air-guide device when the tubular structure is inflated;
  a hose clamp, comprising:
    an encircling element having an inner surface and an opposing outer surface,
    a grabbing component extending from the outer surface of the encircling element, and
    an engaging component disposed on the inner surface of the encircling element,
  wherein the hose clamp is configured to be used at the connection of the tubular structure and the hose.

7. The convective system of claim 6, wherein the separation element comprises a seal surrounding the separation element.

8. The convective system of claim 6, wherein the air-guide device comprises a plurality of staked seals extending from a periphery seal.

9. The convective system of claim 8, wherein at least part of the staked seals are disposed proximate to the longitudinal edge of the tubular structure.

10. The convective system of claim 9, wherein at least part of the staked seals are disposed generally equal spacing along the longitudinal edge.

11. The convective system of claim 6, wherein the encircling element has a first end and a second end, and wherein the engaging component comprises a first set of engaging elements disposed proximate to the first end.

12. The convective system of claim 11, wherein the engaging component further comprises a second set of engaging elements disposed proximate to the second end.

* * * * *